(12) United States Patent
Nishimuta et al.

(10) Patent No.: US 11,786,341 B2
(45) Date of Patent: Oct. 17, 2023

(54) OCCLUSAL BLOCK DESIGN FOR LATERAL LOCKING

(71) Applicant: ALIGN TECHNOLOGY, INC., San Jose, CA (US)

(72) Inventors: James Nishimuta, Durham, NC (US); Jun Sato, San Jose, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

(21) Appl. No.: 17/115,071

(22) Filed: Dec. 8, 2020

(65) Prior Publication Data
US 2021/0169614 A1    Jun. 10, 2021

Related U.S. Application Data

(60) Provisional application No. 62/945,797, filed on Dec. 9, 2019.

(51) Int. Cl.
*A61C 7/36* (2006.01)
*A61C 7/08* (2006.01)

(52) U.S. Cl.
CPC . *A61C 7/36* (2013.01); *A61C 7/08* (2013.01)

(58) Field of Classification Search
CPC .................................................... A61C 7/36
See application file for complete search history.

(56) References Cited

U.S. PATENT DOCUMENTS

| | | |
|---|---|---|
| 5,820,368 A | 10/1998 | Wolk |
| 5,868,138 A | 2/1999 | Halstrom |
| 6,183,248 B1 | 2/2001 | Chishti et al. |
| 6,309,215 B1 | 10/2001 | Phan et al. |
| 6,386,864 B1 | 5/2002 | Kuo |
| 6,454,565 B2 | 9/2002 | Phan et al. |
| 6,471,511 B1 | 10/2002 | Chishti et al. |
| 6,524,101 B1 | 2/2003 | Phan et al. |
| 6,572,372 B1 | 6/2003 | Phan et al. |
| 6,604,527 B1 | 8/2003 | Palmisano |
| 6,607,382 B1 | 8/2003 | Kuo et al. |
| 6,705,863 B2 | 3/2004 | Phan et al. |

(Continued)

FOREIGN PATENT DOCUMENTS

| | | | |
|---|---|---|---|
| DE | 202018103323 U1 * | 7/2018 | |
| KR | 102202863 B1 * | 1/2021 | ........... A61B 17/663 |

(Continued)

OTHER PUBLICATIONS

KR102202863B1 (Chang Wongun, TNS) Orthodontic appliance with mandibular orthopaedic function, Jan. 14, 2021. [retrieved on May 6, 2022], Translation retrieved from: Espacenet (Year: 2021).*

(Continued)

*Primary Examiner* — Amy R Sipp
*Assistant Examiner* — Courtney N Huynh
(74) *Attorney, Agent, or Firm* — FISHERBROYLES, LLP

(57) ABSTRACT

A first appliance and a second appliance comprise engagement surfaces that provide mandibular relocation forces and forces to limit lateral movement of the jaw, such as opposing inclined surfaces on opposite sides of the mouth. In some embodiments, engagement surfaces between oral appliances comprise a curvature difference, which allows engagement at differing angles and positions.

22 Claims, 23 Drawing Sheets

(56) References Cited

U.S. PATENT DOCUMENTS

| | | |
|---|---|---|
| 6,783,604 B2 | 8/2004 | Tricca |
| 6,790,035 B2 | 9/2004 | Tricca et al. |
| 6,814,574 B2 | 11/2004 | Abolfathi et al. |
| 6,830,450 B2 | 12/2004 | Knopp et al. |
| 6,947,038 B1 | 9/2005 | Anh et al. |
| 7,074,039 B2 | 7/2006 | Kopelman et al. |
| 7,104,792 B2 | 9/2006 | Taub et al. |
| 7,121,825 B2 | 10/2006 | Chishti et al. |
| 7,160,107 B2 | 1/2007 | Kopelman et al. |
| 7,192,273 B2 | 3/2007 | McSurdy, Jr. |
| 7,347,688 B2 | 3/2008 | Kopelman et al. |
| 7,354,270 B2 | 4/2008 | Abolfathi et al. |
| 7,448,514 B2 | 11/2008 | Wen |
| 7,481,121 B1 | 1/2009 | Cao |
| 7,543,511 B2 | 6/2009 | Kimura et al. |
| 7,553,157 B2 | 6/2009 | Abolfathi et al. |
| 7,600,999 B2 | 10/2009 | Knopp |
| 7,658,610 B2 | 2/2010 | Knopp |
| 7,766,658 B2 | 8/2010 | Tricca et al. |
| 7,771,195 B2 | 8/2010 | Knopp et al. |
| 7,854,609 B2 | 12/2010 | Chen et al. |
| 7,871,269 B2 | 1/2011 | Wu et al. |
| 7,878,801 B2 | 2/2011 | Abolfathi et al. |
| 7,878,805 B2 | 2/2011 | Moss et al. |
| 7,883,334 B2 | 2/2011 | Li et al. |
| 7,914,283 B2 | 3/2011 | Kuo |
| 7,947,508 B2 | 5/2011 | Tricca et al. |
| 8,152,518 B2 | 4/2012 | Kuo |
| 8,172,569 B2 | 5/2012 | Matty et al. |
| 8,235,715 B2 | 8/2012 | Kuo |
| 8,257,079 B1 | 9/2012 | Plowman |
| 8,292,617 B2 | 10/2012 | Brandt et al. |
| 8,337,199 B2 | 12/2012 | Wen |
| 8,401,686 B2 | 3/2013 | Moss et al. |
| 8,459,267 B2 | 6/2013 | Zimmerman |
| 8,517,726 B2 | 8/2013 | Kakavand et al. |
| 8,562,337 B2 | 10/2013 | Kuo et al. |
| 8,641,414 B2 | 2/2014 | Borovinskih et al. |
| 8,684,729 B2 | 4/2014 | Wen |
| 8,708,697 B2 | 4/2014 | Li et al. |
| 8,758,009 B2 | 6/2014 | Chen et al. |
| 8,771,149 B2 | 7/2014 | Rahman et al. |
| 8,899,976 B2 | 12/2014 | Chen et al. |
| 8,899,977 B2 | 12/2014 | Cao et al. |
| 8,936,463 B2 | 1/2015 | Mason et al. |
| 8,936,464 B2 | 1/2015 | Kopelman |
| 9,022,781 B2 | 5/2015 | Kuo et al. |
| 9,103,338 B2 | 8/2015 | Fukui et al. |
| 9,119,691 B2 | 9/2015 | Namiranian et al. |
| 9,161,823 B2 | 10/2015 | Morton et al. |
| 9,241,774 B2 | 1/2016 | Li et al. |
| 9,326,831 B2 | 5/2016 | Cheang |
| 9,433,476 B2 | 9/2016 | Khardekar et al. |
| 9,610,141 B2 | 4/2017 | Kopelman et al. |
| 9,655,691 B2 | 5/2017 | Li et al. |
| 9,655,693 B2 | 5/2017 | Li et al. |
| 9,655,695 B2 | 5/2017 | Ross |
| 9,675,427 B2 | 6/2017 | Kopelman |
| 9,700,385 B2 | 7/2017 | Webber |
| 9,744,001 B2 | 8/2017 | Choi et al. |
| 9,820,882 B2 | 11/2017 | Liptak et al. |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,299,894 B2 | 5/2019 | Tanugula et al. |
| 10,363,116 B2 | 7/2019 | Boronkay |
| 10,383,705 B2 | 8/2019 | Shanjani et al. |
| D865,180 S | 10/2019 | Bauer et al. |
| 10,449,016 B2 | 10/2019 | Kimura et al. |
| 10,463,452 B2 | 11/2019 | Matov et al. |
| 10,470,847 B2 | 11/2019 | Shanjani et al. |
| 10,492,888 B2 | 12/2019 | Chen et al. |
| 10,517,701 B2 | 12/2019 | Boronkay |
| 10,537,406 B2 | 1/2020 | Wu et al. |
| 10,537,463 B2 | 1/2020 | Kopelman |
| 10,548,700 B2 | 2/2020 | Fernie |
| 10,555,792 B2 | 2/2020 | Kopelman et al. |
| 10,588,776 B2 | 3/2020 | Cam et al. |
| 10,613,515 B2 | 4/2020 | Cramer et al. |
| 10,639,134 B2 | 5/2020 | Shanjani et al. |
| 10,743,964 B2 | 8/2020 | Wu et al. |
| 10,758,323 B2 | 9/2020 | Kopelman |
| 10,781,274 B2 | 9/2020 | Liska et al. |
| 10,813,720 B2 | 10/2020 | Grove et al. |
| 10,874,483 B2 | 12/2020 | Boronkay |
| 10,881,487 B2 | 1/2021 | Cam et al. |
| 10,912,629 B2 | 2/2021 | Tanugula et al. |
| 10,959,810 B2 | 3/2021 | Li et al. |
| 10,993,783 B2 | 5/2021 | Wu et al. |
| 2002/0192617 A1 | 12/2002 | Phan et al. |
| 2003/0031976 A1 | 2/2003 | Clark |
| 2003/0207224 A1* | 11/2003 | Lotte ............... A61C 7/08 433/6 |
| 2004/0166462 A1 | 8/2004 | Phan et al. |
| 2004/0166463 A1 | 8/2004 | Wen et al. |
| 2005/0014105 A1 | 1/2005 | Abolfathi et al. |
| 2005/0028826 A1* | 2/2005 | Palmisano ........... A61F 5/566 128/848 |
| 2005/0186524 A1 | 8/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0115782 A1 | 6/2006 | Li et al. |
| 2006/0115785 A1 | 6/2006 | Li et al. |
| 2006/0166158 A1 | 7/2006 | Abels et al. |
| 2006/0199142 A1 | 9/2006 | Liu et al. |
| 2006/0234179 A1 | 10/2006 | Wen et al. |
| 2007/0283967 A1* | 12/2007 | Bailey ............... A61F 5/566 128/848 |
| 2008/0118882 A1 | 5/2008 | Su |
| 2008/0160473 A1 | 7/2008 | Li et al. |
| 2008/0268400 A1 | 10/2008 | Moss et al. |
| 2008/0286716 A1 | 11/2008 | Sherwood |
| 2008/0286717 A1 | 11/2008 | Sherwood |
| 2009/0280450 A1 | 11/2009 | Kuo |
| 2010/0055635 A1 | 3/2010 | Kakavand |
| 2010/0129763 A1 | 5/2010 | Kuo |
| 2011/0269092 A1 | 11/2011 | Kuo et al. |
| 2014/0067334 A1 | 3/2014 | Kuo |
| 2015/0238280 A1* | 8/2015 | Wu ............... A61C 7/002 433/24 |
| 2015/0265376 A1 | 9/2015 | Kopelman |
| 2015/0366637 A1 | 12/2015 | Kopelman et al. |
| 2015/0366638 A1 | 12/2015 | Avi et al. |
| 2016/0193014 A1 | 7/2016 | Morton et al. |
| 2016/0199216 A1 | 7/2016 | Cam et al. |
| 2016/0242870 A1 | 8/2016 | Matov et al. |
| 2016/0242871 A1 | 8/2016 | Morton et al. |
| 2016/0361139 A1* | 12/2016 | Webber ............. A61C 13/0004 |
| 2017/0007359 A1 | 1/2017 | Avi et al. |
| 2017/0007360 A1 | 1/2017 | Kopelman et al. |
| 2017/0007361 A1 | 1/2017 | Allen et al. |
| 2017/0007365 A1 | 1/2017 | Kopelman et al. |
| 2017/0007366 A1 | 1/2017 | Kopelman et al. |
| 2017/0007386 A1 | 1/2017 | Mason et al. |
| 2017/0035533 A1* | 2/2017 | Ross ............... A61C 7/36 |
| 2017/0135792 A1 | 5/2017 | Webber |
| 2017/0135793 A1 | 5/2017 | Webber et al. |
| 2017/0165032 A1 | 6/2017 | Webber et al. |
| 2017/0319296 A1 | 11/2017 | Webber et al. |
| 2018/0078344 A1* | 3/2018 | Falkel ............... A61C 7/36 |
| 2018/0147028 A1 | 5/2018 | Warshawsky et al. |
| 2018/0153648 A1 | 6/2018 | Shanjani et al. |
| 2018/0153733 A1 | 6/2018 | Kuo |
| 2018/0168776 A1 | 6/2018 | Webber |
| 2018/0353264 A1 | 12/2018 | Riley et al. |
| 2018/0360567 A1 | 12/2018 | Xue et al. |
| 2018/0368944 A1 | 12/2018 | Sato et al. |
| 2019/0000592 A1 | 1/2019 | Cam et al. |
| 2019/0000593 A1 | 1/2019 | Bruce et al. |
| 2019/0021817 A1 | 1/2019 | Sato et al. |

(56) References Cited

U.S. PATENT DOCUMENTS

| | | |
|---|---|---|
| 2019/0029775 A1 | 1/2019 | John et al. |
| 2019/0046297 A1 | 2/2019 | Kopelman et al. |
| 2019/0069975 A1 | 3/2019 | Cam et al. |
| 2019/0099129 A1 | 4/2019 | Kopelman et al. |
| 2019/0125494 A1 | 5/2019 | Li et al. |
| 2019/0125497 A1 | 5/2019 | Mitra et al. |
| 2019/0152152 A1 | 5/2019 | O'Leary et al. |
| 2019/0175304 A1 | 6/2019 | Morton et al. |
| 2019/0231477 A1 | 8/2019 | Shanjani et al. |
| 2019/0262101 A1 | 8/2019 | Yaser et al. |
| 2019/0298494 A1 | 10/2019 | Webber et al. |
| 2019/0314119 A1 | 10/2019 | Kopelman et al. |
| 2019/0338067 A1 | 11/2019 | Robert et al. |
| 2019/0343606 A1 | 11/2019 | Wu et al. |
| 2020/0000553 A1 | 1/2020 | Svetlana et al. |
| 2020/0086553 A1 | 3/2020 | Mojdeh et al. |
| 2020/0100864 A1 | 4/2020 | Yuxiang et al. |
| 2020/0100865 A1 | 4/2020 | Yuxiang et al. |
| 2020/0100866 A1 | 4/2020 | Viktoria et al. |
| 2020/0100871 A1 | 4/2020 | Yuxiang et al. |
| 2020/0155276 A1 | 5/2020 | Bruce et al. |
| 2020/0188062 A1 | 6/2020 | Avi et al. |
| 2020/0214598 A1 | 7/2020 | Huizhong et al. |
| 2020/0214801 A1 | 7/2020 | Yuxiang et al. |
| 2020/0390523 A1 | 12/2020 | Sato et al. |
| 2021/0078357 A1 | 3/2021 | Venkatasanthanam et al. |

FOREIGN PATENT DOCUMENTS

| | | | |
|---|---|---|---|
| WO | WO-2006096558 A2 * | 9/2006 | ............... A61C 7/00 |
| WO | 2017106896 A1 | 6/2017 | |
| WO | 2019213585 A1 | 11/2019 | |
| WO | 2019213588 A1 | 11/2019 | |

OTHER PUBLICATIONS

DE202018103323U1 (Schlieper Joerg) Unterkieferprotrusionseinrichtung, Jun. 20, 2018. [retrieved on Oct. 14, 2022], Translation retrieved from: Espacenet (Year: 2018).*

* cited by examiner

OCCLUSAL BLOCK DESIGN FOR LATERAL LOCKING

RELATED APPLICATIONS

This application claims the benefit under 35 U.S.C. § 119(e) of U.S. Provisional Patent Application No. 62/945,797, filed Dec. 9, 2019, and titled "OCCLUSAL BLOCK DESIGN FOR LATERAL LOCKING," which is incorporated, in its entirety, by this reference.

BACKGROUND

The present disclosure is generally related to the treatment of malocclusions with oral appliances, such as devices for mandibular relocation and methods of use.

Dental treatments may involve procedures for repositioning misaligned teeth and changing bite configurations for improved cosmetic appearance and/or dental function. Repositioning can be accomplished, for example, by applying controlled forces to one or more teeth over a period of time.

As an example, orthodontic repositioning may be provided through a dental process that uses positioning appliances for repositioning teeth. Such appliances may utilize a thin shell of material having resilient properties, referred to as an "aligner," that generally conforms to a patient's teeth and applies tooth repositions forces to incrementally repositions the patient's teeth.

Placement of such an appliance over the teeth may provide controlled forces in specific locations to gradually move the teeth into a new configuration. Repetition of this process with successive appliances in progressive configurations can move the teeth through a series of intermediate arrangements towards a final arrangement.

Such systems typically utilize materials that are light weight and/or transparent to provide as a set of appliances that can be used sequentially in stages such that as the teeth move in response to the treatment, a new appliance for a new state of treatment of can be implemented to further move the teeth without having to take a new impression of the patient's teeth at every increment of tooth movement in order to make the successive appliance.

In various instances, teeth of a patient's upper jaw and teeth of the patient's lower jaw may contact in an incorrect or suboptimal manner (e.g., crowding, crossbite, deep bite). A proper fit of the occlusal surfaces of the teeth is helpful for proper biting and chewing, as well as desirable for aesthetic appearance. Otherwise, premature wear of the teeth, undesirable flexion of the teeth, and/or undesirable forces on dental restorations may be experienced by the patient. For instance, a proper fit can be a function of the relative positions of teeth and the mandible and maxilla, either of which may be retruded or protruded relative to the ideal position. The maxilla (e.g., the upper jaw) is a bone that is fixed to the skull. The mandible (e.g., lower jaw) is a bone that is attached to the skull by numerous muscles which guide its movement. The mandible articulates at its posterior upward extremities with the temporal bone to form the jaw joint. The jaw joint is a loosely connected joint that accommodates the variety of movements of the mandible relative to the maxilla during biting and chewing motions. The numerous muscles attaching the mandible to the skull control and power the complex movements involved in biting and chewing. Because the condylar relationship affords some flexibility in the positioning of the jaw, the lower jaw can be intentionally repositioned in accordance with the fit of the teeth, for instance, by using an oral appliance.

Prior approaches to mandibular repositioning can be less than ideal in at least some respects. For example, at least some of the prior devices that extend between teeth or to the sides of the teeth can be somewhat larger and less comfortable for the patient than would be ideal. For example, oral appliances that rely on the jaws closing to reposition the mandible may allow less than ideal jaw closure. Also, work in relation to the present disclosure suggests that the contacting surfaces of the prior oral appliances may less than ideally suited to accommodate variability on the patient's mouth. The prior structures relied upon to transmit of forces between the upper and lower jaws to reposition the mandible can provide somewhat indirect forces, which can be related to undesirable mandibular movement. Also, the manufacturing of at least some of the prior oral appliances for mandibular relocation can be somewhat more complex to design and manufacture than would be ideal.

In light of the above, improved mandibular relocation devices that overcome at least some of the above limitations of the prior devices would be helpful.

SUMMARY

Embodiments of the present disclosure provide improved oral appliances for mandibular relocation with improved engagement that can allow improved jaw closure, less undesirable jaw movement and decreased complexity. In some embodiments, a first appliance and a second appliance of a first stage of treatment comprise engagement surfaces that provide mandibular relocation forces and forces to limit lateral movement of the jaw, such as opposing inclined surfaces on opposite sides of the mouth. In some embodiments, engagement surfaces between oral appliances comprise a curvature difference, which allows engagement at differing angles and positions. The curvature difference can also facilitate the design and manufacturing of the oral appliances because the engagement surfaces can be brought into engagement at various angles with respect to each other. In some embodiments, the engagement between a first appliance and a second appliance occurs at a locus of engagement that can vary across the engagement surfaces as the draws are drawn toward each other, which can provide a more continuous movement and change in mandibular relocation forces as the jaws are drawn toward each other. Also, the curvature difference can allow the engagement structures to have decreased height within the mouth of the patient, which can provide more direct engagement between the upper and lower jaws of a patient.

In some embodiments, the first appliance and the second appliance comprise a plurality of replicated occlusal blocks, which can facilitate design of the oral appliances and manufacturing. The plurality of replicated occlusal blocks may comprise a curvature difference that allows the replicated blocks to engagement with each other at various angles to accommodate individual variability of the patient's mouth, such as variability associated with a Curve of Spee. In some embodiments, each of the plurality of replicated occlusal blocks comprises a curvature difference across the engagement surface, which allows the blocks to engage each other when flipped in orientation. The plurality of replicated occlusal blocks can be placed at a plurality of locations on the appliances to engage each other, which can facilitate design and manufacturing at the plurality of locations.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

Figure 1:
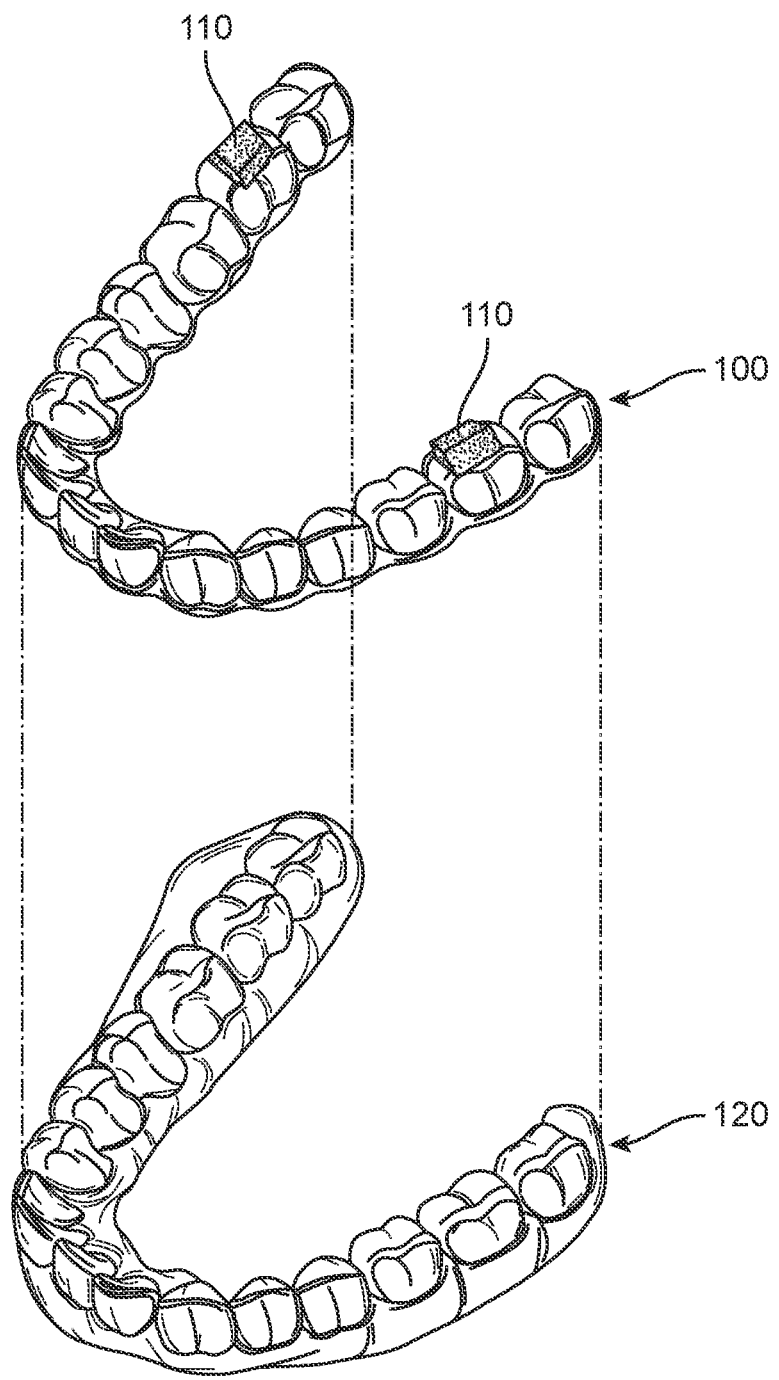
FIG. 1 shows an oral appliance and engagement structures, in accordance with some embodiments.

The following detailed description provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The methods, apparatus, oral appliances and occlusal blocks disclosed herein are well suited for combination with prior devices such as aligners to reposition teeth, for example the Invisalign™ system commercially available from Align Technology, Inc. For example, a plurality of appliances can be sequentially placed for tooth movement at different incremental sequential stages of treatment and for mandibular relocation either in combination with tooth movement stages or separate stages for mandibular relocation. Also, the presently disclosed engagement structures and occlusal blocks are well suited for incorporation into prior devices for mandibular relocation to provide decreased size and improved engagement. For example, the presently disclosed engagement structures can be combined with one or more features of Precision Wings.

The presently disclosed methods and apparatus are well suited for combination with prior approaches to manufacturing aligners, such as with direct fabrication and overmolding such as thermoforming. For example, the presently disclosed occlusal blocks can be placed on a positive mold of the patient's dentition, and one or more polymeric layers of material thermoformed over the occlusal blocks. Also, the occlusal blocks are well suited for additive manufacturing such as 3D printing. The plurality of occlusal blocks as described herein can be repeatedly placed on a computer model of the patient's mouth to facilitate design of mandibular relocation appliances. Also, the repeated placement and decreased size can decrease the amount of additive manufacturing material and decrease manufacturing time, for example when the appliance is directly fabricated as a single part with the thin polymeric shell and occlusal blocks together, or when the occlusal blocks are manufactured separately and thermoformed.

The present disclosure describes appliances and structures for mandibular relocation, including treating class II malocclusions, class III malocclusions, and sleep apnea correction. An oral appliance for insertion into the mouth of a patient may comprise a plurality of occlusal blocks and engagement structures for generating mandibular relocation forces and positioning. The appliance may include teeth receiving cavities for fitting over the teeth of a patient, such as with an orthodontic aligner. A plurality of occlusal blocks is provided with the appliance and promote mandibular relocation, such as by promoting mandibular advancement, retraction, lateral correction, or a combination.

The occlusal blocks cooperate to align the mandible with the maxilla according to a treatment profile. For example, a first occlusal block can be associated with an appliance coupled to upper teeth of a patient, and a second occlusal block can be associated with an appliance coupled to lower teeth of a patient. The first and second occlusal blocks may be located to interfere with one another to maintain the mandible in a desired position, such as be interfering with retraction, advancement, or lateral movement of the mandible once the mandible is properly located.

The occlusal blocks may have engagement surfaces in which a first occlusal block on a first appliance engages a second occlusal block on a second appliance. The engagement surfaces apply forces on the mandible to correct for class II malocclusions, class III malocclusions, or other types of misalignment of the mandible.

The occlusal blocks may have the same geometry and may be configured to be installed in any portion of the mouth of a patient to provide the features and benefits described herein. The appliances formed with the occlusal blocks may comprise engagement surfaces for contacting each other with engagement surfaces similar to the surfaces of the occlusal blocks as described herein.

FIG. 1 shows an oral appliance 100 and one or more engagement structures 110 carried by the appliance 100. The appliance 100 can be configured to fit over an entire dental arch 120. In other embodiments, the oral appliance may be designed to fit over some or all of the teeth in the upper or lower jaw. For example, the dental appliance 100 may be formed with a plurality of teeth receiving cavities that allow the oral appliance 100 to securely fit onto the dental arch. The oral appliance 100 can be fabricated from a polymeric shell, or formed from another material, and include a number of teeth receiving cavities shaped to receive corresponding teeth. Aligners for positioning teeth are commercially available from Align Technology.

The one or more engagement structures 110 can be place at any suitable location of the oral appliance 100, but according to some embodiments, corresponding pairs of engagement structures 110 are placed on the appliance 100 associated with the upper jaw of a patient and on an appliance associated with the lower jaw of a patient. In some embodiments, the corresponding pairs of engagement structures 110 reposition the lower jaw relative to the upper jaw. For example, the lower jaw may be repositioned anteriorly (e.g., correcting for retrognathism), posteriorly (e.g., correcting for prognathism), or laterally with respect to the upper jaw. Accordingly, the corresponding pairs of engagement structures can be used with an oral appliance to address class 1, class 2, or class 3 malocclusions in a patient.

The oral appliance comprises suitable materials for use with an oral appliance. The oral appliance may be made of any suitable material as will be appreciated by one of ordinary skill in the art. In some embodiments, the engagement structures 110 may be formed into the oral appliance, such as by overmolding, for example. As an example, one or more engagement structures 110 may formed by placing an occlusal block as described herein on a positive mold of a patient's dentition, and an overmold material, which may be any of a number of suitable polymers, is molded over the one or more engagement structures 110 and the positive mold. The result is an oral appliance 100 that comprises a plurality of teeth receiving cavities and the one or more engagement structures 110 with the occlusal blocks as described herein embedded within the oral appliance 100, for example.

While the description may refer to a first appliance and a second appliance, it should be understood that referring to the appliances with this nomenclature is not intended to indicate a position of the appliance within the mouth of a patient. For instance, a first appliance may be configured to fit over the upper dental arch of a patient or may be configured to fit over the lower dental arch of a patient. Similarly, reference to a first engagement structure, second engagement structure, third engagement structure, or fourth engagement structure does not, by itself, indicate a position within the mouth of a patient, or a location on a particular oral appliance, unless specified.

Figure 2A:
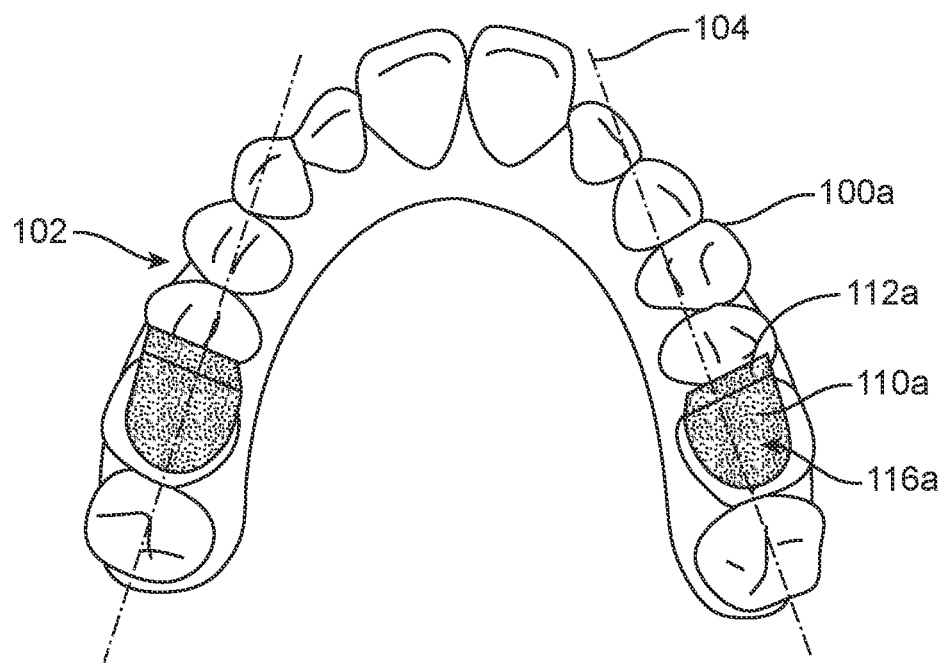
FIG. 2A shows a pair of engagement structures associated with an upper dental appliance, in accordance with some embodiments.
Figure 2B:
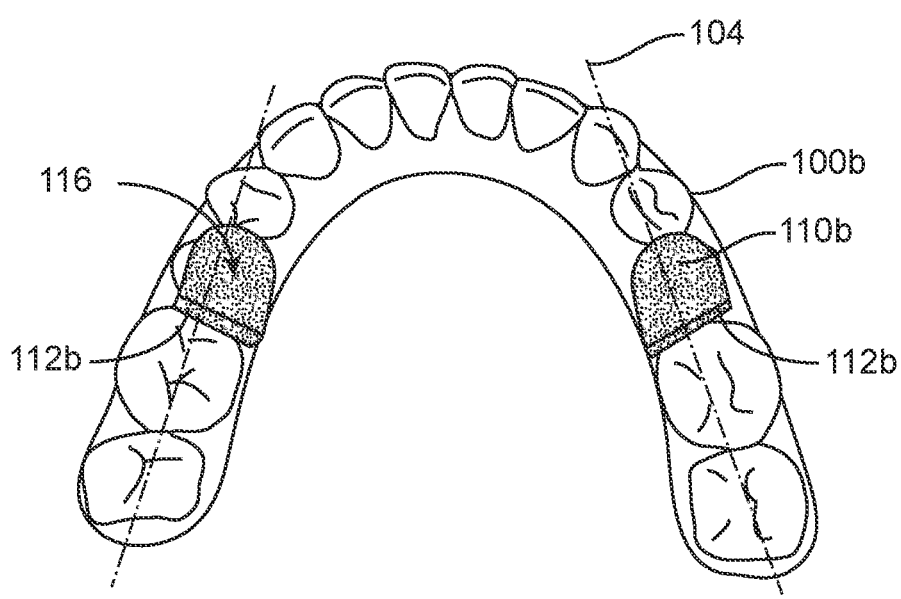
FIG. 2B shows a pair of engagement structures associated with a lower dental appliance, in accordance with some embodiments.
Figure 2C:
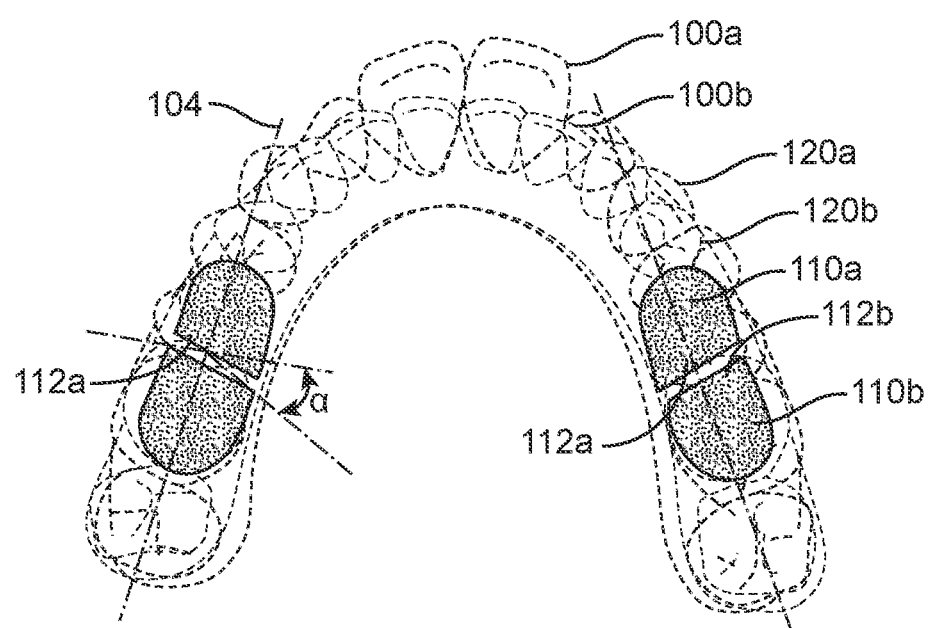
FIG. 2C shows a schematic representation of an example relative positioning of the upper engagement structures and the lower engagement structures, in accordance with some embodiments.

FIGS. 2A, 2B and 2C illustrate cooperating pairs of engagement structures associated with an upper dental appliance 100a along an upper dental arch 120a and a lower dental appliance 100b along an lower dental arch 120b, in accordance with some embodiments. The upper dental appliance 100a defines a plurality of teeth cavities sized and shaped to fit over the teeth of a patient. A pair of engagement structures 110a may be shaped, embedded, attached, affixed, or otherwise carried by the upper dental appliance 100a, and may comprise occlusal blocks as described herein. In some embodiments, the engagement structures 110a and corresponding occlusal blocks have a midline 104 that divides the engagement structure into a left and a right side. The engagement structures have an occlusal surface that faces generally away from the dentition on which appliance is placed. When in use, the occlusal surface 116a of an engagement structure associated with an upper appliance will be oriented generally toward the lower appliance. Similarly, the occlusal surface of an engagement structure associated with a lower appliance will typically face toward the engagement structure of upper appliance when in use by a patient.

In some embodiments, the engagement structure 110a and corresponding occlusal block have an engagement surface 112a that is generally inclined in relation to the occlusal surface. It should be appreciated that the engagement surface can be sized and shaped in many ways and may be curved, contoured, shaped, or sloped, for example. In some embodiments, as illustrated in FIG. 2A, where the engagement structure is outfitted to an upper oral appliance for placement on maxillary teeth, the engagement surface may face generally anteriorly (e.g., toward the front of the mouth, where the incisors are located).

In some embodiments, such as is illustrated in FIG. 2B, where the engagement structure 110b is associated with a lower oral appliance 100b for placement on mandibular teeth, the engagement surface 112b may face generally posteriorly. When arranged as illustrated in FIGS. 2A and 2B, the engagement surfaces 112a, 112b may cooperate to aid with mandible relocation. For example, as illustrated, the first engagement structure 110a may be located on an upper appliance 100a, as shown in FIG. 2A, while a second engagement structure 110b may be located on a lower appliance 100b, as shown in FIG. 2B. In use, where the appliances 100 are fitted to the dentition of a patient, as the patient bites down, the lower jaw comes forward (e.g., mandible advancement), and the engagement surfaces 112 associated with engagement structures of the upper appliance and lower appliance touch one another and interfere to provide mandibular relocation. In some embodiments, the mandible is urged toward more forward position, which helps in correcting an overbite of the patient. In addition, the engagement surfaces may also help to reduce lateral movement, e.g., side to side movement of the lower jaw, which can promote mandibular relocation.

In some embodiments, the engagement structures are positioned and oriented to promote the mandible in a more rearward position. That is, the engagement structures may assist with retracting the mandible to assist in correcting an underbite of the patient, for example.

Figure 3:
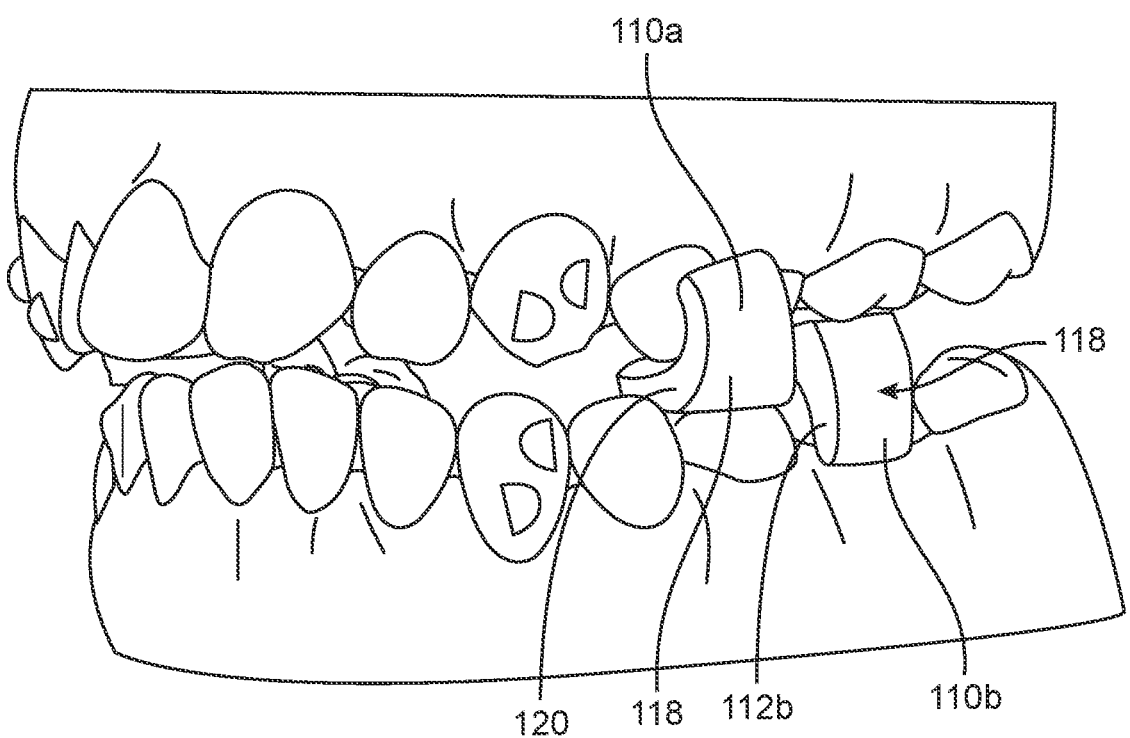
FIG. 3 shows pair of engagement structures for repositioning a mandible and reducing lateral movement, in accordance with some embodiments.

FIG. 3 shows a schematic representation of an example relative positioning of the upper engagement structures and the lower engagement structures, in accordance with some embodiments. In some embodiments, the engagement structures can be positioned and configured to correct retrognathism, e.g., underbite, or may be positioned and configured to correct for prognathism, e.g. overbite. By way of example, the configuration will be described as promoting mandibular advancement, although the engagement structure can be interchanged to provide mandibular retraction.

As shown, a pair of first engagement structures are associated with a lower appliance and can be placed on a lower dentition of a patient. A pair of second engagement structures may be associated with an upper appliance and can be placed on an upper dentition of a patient. In use, once the upper appliance and lower appliance are placed onto the dentition of a patient, as the appliances are brought together, the engagement structures contact each other. As the mandible is advanced, the patient is able to bite down and bring the upper appliance and lower appliance together. Once a patient bites down, the first engagement structures and the second engagement structures reduce the ability of the mandible to retract from a forward position.

As shown, the first engagement structure has a midline that partitions the first engagement structure into a first side and a second side, e.g. a left side and a right side. In some embodiments, the first engagement surface is inclined with respect to the midline at an angle. In some embodiments, this angle of inclination a is about 5 degrees, 10 degrees, 15 degrees, 20 degrees, 30 degrees, 40 degrees, or 45 degrees, or within a range defined by any two of the preceding values. In some embodiments, the angle $\alpha$ is within the range from about 10 degrees to about 25 degrees.

In some embodiments, the angle of inclination a provides support to help position the mandible in a forward position, and in addition, provides support to limit lateral movement as the first engagement surface contacts the second engagement surface at a locus of engagement. For example, the left and right sides of the appliances may comprise opposing engagement structures so as to limit lateral jaw movement while providing mandibular advancement forces. For example, a first engagement structure and a second engagement structure on first side of the appliances on a first side of the mouth may contact each other with a corresponding angle of inclination so as to generate first a lateral force associated with a first mandibular advancement force. A first engagement structure and a second engagement structure on a second side of the appliances on a second side of the mouth may contact each other with a corresponding angle of inclination so as to generate a second lateral force associated with a second mandibular advancement force. In some embodiments, the first and second forces are oppositely oriented and can help to maintain the mandible in position and decrease lateral movement so as to promote mandibular relocation.

FIG. 3 illustrates a pair of engagement structures 110 for repositioning a mandible and reducing lateral movement, which may be incorporated into an upper appliance and a lower appliance as described herein. In the illustrated configuration, a first engagement structure 110a is associated with a mandible on a mandibular appliance and a second engagement structure 110b is associated with a maxilla on a maxillary appliance. The first engagement structure has an occlusal portion 120 and a buccal portion 118. The occlusal portion of the first engagement structure 110b located on an appliance as described herein so as to be located generally adjacent the occlusal surface of a lower tooth or teeth when the appliance has been placed on the lower teeth. When the appliance has been placed on the lower teeth, the occlusal portion of the first engagement structure 110a is located between the upper dentition and lower dentition. The buccal portion 118 is positioned adjacent the buccal surface of the tooth or teeth and is between the teeth and cheek, for example when located near a molar or premolar tooth. Although reference is made to a buccal portion, the appliance may comprise a lingual portion extending from the occlusal portion to a lingual side of the patient's teeth.

The occlusal portion 120 and buccal portion 118 each define an engagement structure 110 comprising an engagement surface 112 that is configured to engage a corresponding engagement surface 112 on a cooperating engagement structure 110, such as the second engagement structure 110a. The engagement surface may be as described herein, and may be inclined with respect to a midline of the engagement structure. In some embodiments, the engagement surface is substantially perpendicular to the midline of the engagement structure and the limitation on lateral movement may be provided solely by the buccal portion. As illustrated, the first engagement structure may be associated with the mandible, that is, the first engagement structure may be attached or embedded within a first appliance for placement on the lower dentition and the buccal portion extends proximate to and engages the buccal surface of one or more teeth of the maxilla. The second engagement structure may be associated with the maxilla, that is, the second engagement structure may be attached or embedded within a second appliance for placement on the upper dentition and the buccal portion extends proximate to and engages the buccal surface of one or more teeth of the mandible. In this configuration, lateral movement of the mandible relative to the maxilla is reduced.

Figure 4A:
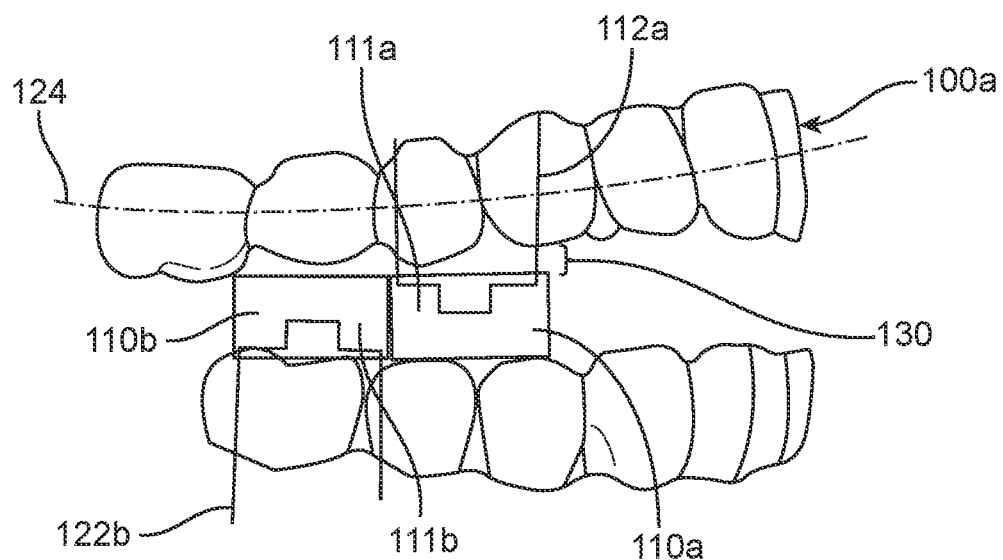
FIG. 4A shows a pair of engagement structures for repositioning a mandible with a gap formed between the teeth and the engagement structure, in accordance with some embodiments.

FIG. 4A shows a pair of engagement structures 110 for repositioning a mandible with a gap 130 formed between the teeth and the engagement structure 110. A first occlusal block 111a may be secured to a first appliance 100a for placement on the dentition of a patient. The first occlusal block 111a can be carried by the first oral appliance 100a for placement on the teeth as described herein. The first appliance 100a can be coupled to the first occlusal block 111a during appliance fabrication, such as by overmolding, e.g. thermoforming, the thin layer of appliance material onto the first occlusal block to form the first engagement structure, for example. As can be seen in FIG. 4A, there may be a gap 130 between the maxilla of a patient and the first engagement structure 110a. This may be related to, at least in part, by the shape of the first engagement structure 110a and the second engagement structure 110b. For example, with flat surfaces the engagement between the surfaces is generally intended to provide contact along the flat surfaces. This engagement between flat surfaces can be related to constraints in the angle of the occlusal blocks with respect to each other, such as when the occlusal surfaces of the teeth correspond to a curved surface.

During manufacturing of appliances, a first base can be provided on a positive mold of the first teeth and the first occlusal block received on the first base. The appliance can be overmolded, e.g. thermoformed, on the first positive mold, the first base and the first occlusal block to form the first appliance. The first appliance is removed from the positive mold and base with the first occlusal block attached thereto. When placed on the teeth of the patient, a gap 130 may extend between the first appliance and the first occlusal block. The second appliance can be similarly fabricated with a second positive mold, a second base, and a second occlusal block.

In at least some instances, the dentition exhibits a curvature in at least two dimensions, such as along the occlusal surfaces such that the occlusal surfaces do not extend along an occlusal plane. For example, the upper dentition and lower dentition may follow a dental arch, and in addition, one or more of these may be curved along the occlusal surfaces with a curve known as the Curve of Spee 124 as illustrated in FIG. 4A. In some embodiments, the engagement structures will have a tendency to align with one another, such as where they form a surface-to-surface contact along flat engagement surfaces. Although one or more of the occlusal blocks can be inclined with respect to the occlusal surfaces of the teeth, this can create a gap 130, for example between the upper engagement structure and the upper dentition as shown in FIG. 4A. Work in relation to the present disclosure suggests that reinforcement structures can be provided on the appliance proximate the gap in order to reinforce the appliance near the gap.

Work in relation to the present disclosure suggests that flat surface contact may impart forces onto the first and/or second engagement structure that may bias one or more of the engagement structures away from the dentition. This bias may be accounted for by altering the contact surfaces of the engagement structures to reduce applied forces that tends to draw one or more of the engagement structures away from the dentition, this solution may rely on individually designed engagement structures for each application and for individual patients. For example, custom occlusal blocks can be manufactured as described herein to fill the gap shown in FIG. 4A, so as to extend from the appliance to the occlusal surface of one or more teeth on which the appliance is to be placed so as to fill the gap.

Figure 4B:
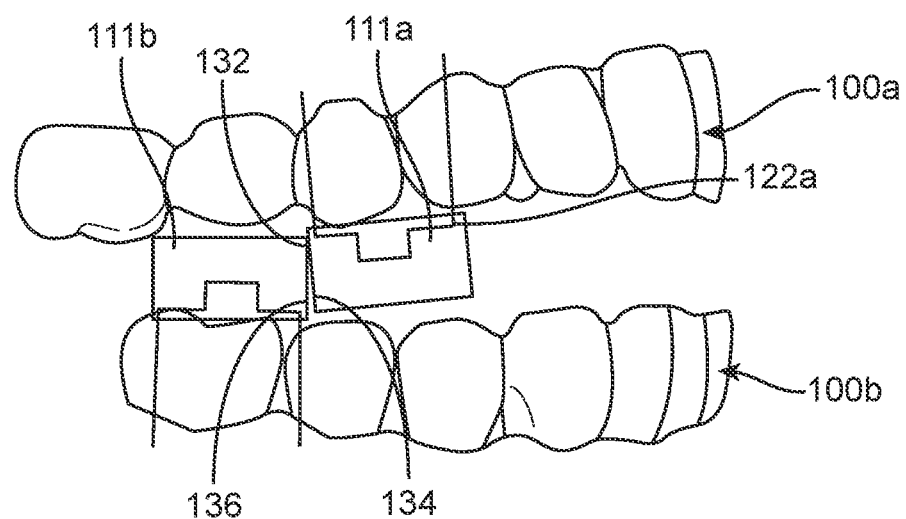
FIG. 4B shows a pair of engagement structures for repositioning a mandible with a curved engagement surface to allow the engagement structure to follow the Curve of Spee while providing a locus of engagement, in accordance with some embodiments.

FIG. 4B shows a pair of engagement structures for repositioning a mandible with one or more curved engagement surfaces. According to some embodiments, providing one or more curved engagement surfaces allows variation in the angle of engagement between the engagement structures and can allow the engagement structure to follow the Curve of Spee 124. This can allow the occlusal blocks 111 to a placed in proximity to the underlying one or more teeth. In some embodiments, the one or more curved surfaces provide a locus of engagement 132 that reduces forces on the engagement structures that may tend to bias the engagement structures away from the dentition, for example. The one or more curved surfaces 134 may comprise a curved surface of a first occlusal block and a flat surface 136 of a second occlusal block that engage each other at a locus of engagement.

In some embodiments, the appliances worn by the patient are formed by overmolding, such as thermoforming. For example, the first appliance can be manufactured by placing a first occlusal block on a first base on a first positive mold of first teeth of a patient and thermoforming the thin polymeric layer of material over the first positive mold of the teeth, the first base 122a and the first occlusal block. The first appliance can be removed with the first occlusal block attached thereto and subjected to additional manufacturing steps as described herein. The second appliance can be similarly manufactured. The first and second appliances can be placed on the first and second teeth to provide engagement as illustrated in FIG. 4B.

In some embodiments, the locus of engagement approximates a line of contact that extends between the first engagement structure and the second engagement structure. Depending on the material used for the occlusal block and appliance material such as thermoformed material, the engagement structures may deform in response to contact therebetween, which may alter the locus of engagement. The one or more curved engagement surfaces can allow the engagement structures to slide with respect to each other, such that the locus of engagement moves as the jaws are drawn together.

While the locus of engagement may approximate and extend along a line of contact, it should be appreciated that the locus of engagement may comprise one or more of many shapes, such as rectangular, oval or butterfly shaped. In some embodiments the locus of engagement is bounded by a rectangle having a high width to height aspect ratio, such as 3:1, 5:1, 8:1, 10:1, or greater. In other words, the locus of engagement may approximate a rectangle having a width substantially greater than its height.

In embodiments in which one of a pair of engagement structures includes a curved engagement surface, it can be located depending on the oral geometry of the patient. For example, in some patients, the Curve of Spee 124 is generally convex, which may facilitate locating an engagement structure with a curved engagement surface on the maxilla. In some cases, the Curve of Spee 124 may be concave, which may facilitate locating an engagement block with curved engagement surface on the mandible, for example. In some embodiments, a cooperating pair of engagement structures (e.g., one associated with the maxilla, and one associated with the mandible), have different geometries. The differing geometries may assist in proper placement. In some instances, a pair of cooperating engagement structures have similar, or even identical, geometries. In some embodiments, the engagement surface of cooperating engagement structures is different, such as is illustrated in FIG. 4B.

Figure 5:
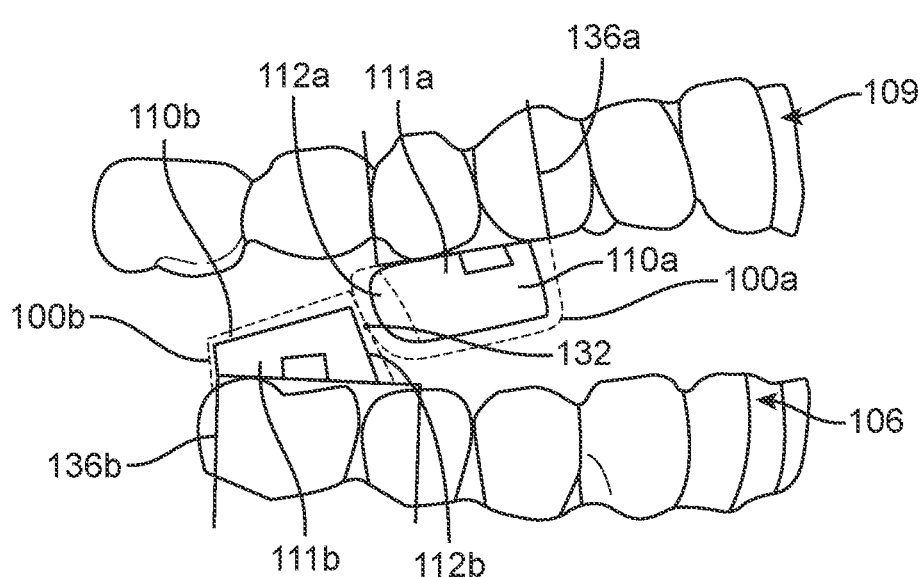
FIG. 5 shows a pair of engagement structures associated with an upper appliance and a lower appliance, in accordance with some embodiments.

FIG. 5 shows a pair of engagement structures 110 associated with an upper appliance 100a for a maxillary arch 109 and a lower appliance 100b for a mandibular arch 106, in accordance with some embodiments. The first engagement structure 110a may be associated with a first appliance 100a. In some embodiments, the first appliance 100a comprises a first engagement structure 110a, and the first engagement structure 110a comprises a first occlusal block 111a and the layer of appliance material covering the first occlusal block. In some embodiments, the second appliance 100b comprises a second engagement structure 110b, and the second engagement structure 110b comprises a second occlusal block 111b and the layer of appliance material covering the second occlusal block. For example, the engagement structure 110a of the first appliance may comprise a portion of the appliance material covering the first occlusal block 111a and the engagement structure of the second appliance 110b may comprise a portion of the appliance material covering the second occlusal block 111a, in which contact of the first and second appliance surfaces at the locus of engagement 132 transmits forces to the underlying occlusal blocks 111 and teeth.

The first and second appliances 100 can be manufactured as described herein. In some embodiments, the first base 136a is located on a positive mold of one or more maxillary teeth of a patient, such as one or more molars, premolars, or a combination, by any suitable method or technique. The first occlusal block 111a may be coupled to the first base 136a in any suitable way, such as by an interference fit, a key and keyhole fit, a boss and pocket, or any other suitable type of connection. The second occlusal block 111b may be similarly coupled to the second base 136b, for example.

The first and second engagement structures 110 may have different shapes and may have different engagement surfaces. In some embodiments, the first engagement structure 110a has a first engagement surface 112a that is contoured (e.g., curved, shaped, profiled, or something other than a flat surface). The second engagement structure 110b has a second engagement surface 112b that cooperates with the first engagement surface to aid in mandibular alignment. The second engagement surface 112b may be substantially flat, or may be contoured and configured to cooperate with the first engagement surface. Where a curved surface meets a flat surface, the locus of engagement may approximate a line. In some embodiments, the engagement structure comprises an occlusal block embedded within the associated appliance, which may be formed of a material as described herein. Accordingly, as a first appliance contacts a second appliance, the appliances my elastically deform and modify the locus of engagement, which may be dependent on the forces between the engagement structures. For example, as the force between the engagement structures increases, the area of the locus of engagement may increase as the corresponding appliances elastically deform in response to the contact force. The occlusal blocks of each appliance can transmit forces from the other appliance to one or more teeth in contact with each occlusal block.

In some embodiments, configuring the engagement structures to have a smaller locus of engagement, such as one approximating a line, allows one of more of the first or second engagement structure to be positioned closer to the associated teeth. This allows the height of each engagement structure to be reduced as well as reduces a possible gap between the engagement structure and the associated teeth, which can result in improved force transmission between the jaws with a smaller height structure on each of the occlusal blocks. In some embodiments, this may allow the jaws to be drawn closer together and may result in improved patient comfort and experience.

Figure 6:
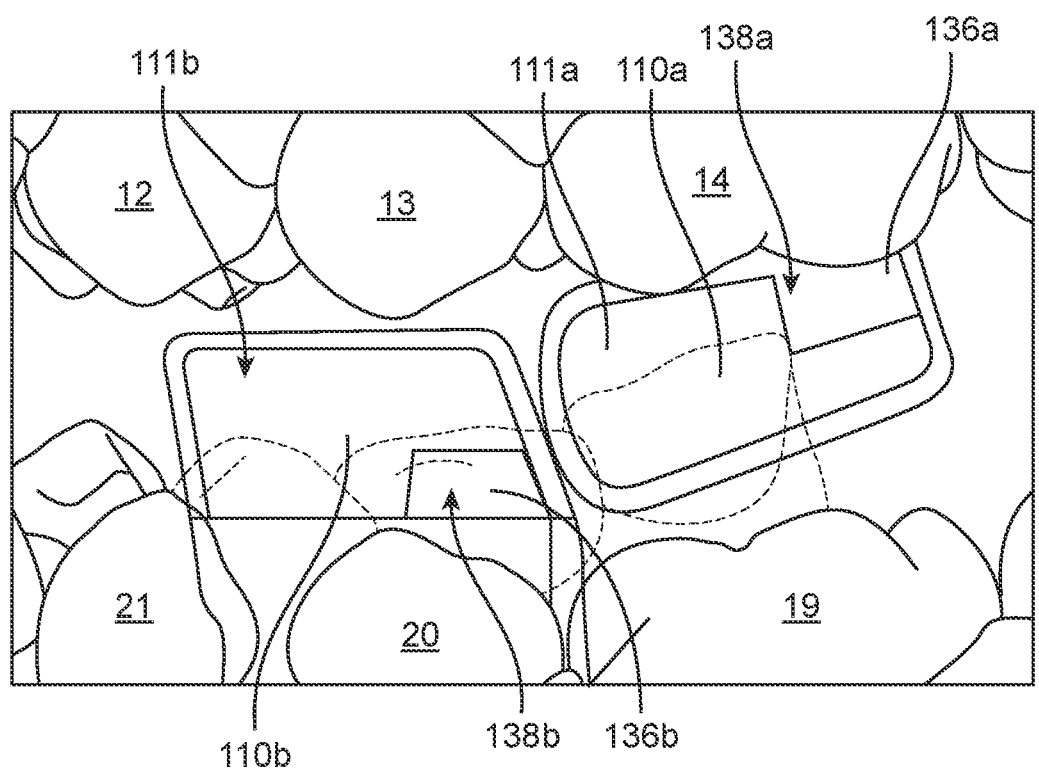
FIG. 6 shows a pair of engagement structures associated with an upper appliance and a lower appliance utilizing a keyed positioning system, in accordance with some embodiments.

FIG. 6 shows a pair of engagement structures 110 associated with an upper appliance and a lower appliance utilizing a keyed positioning system, in accordance with some embodiments. A first base 136a may be attached to a positive mold of one or more maxillary teeth of a patient. The first key 138a may comprise a boss, or a key, or other structure that helps determine the location of first occlusal block and corresponding a first engagement structure. For example, the first base 136a may be attached to a positive mold of a maxillary tooth through any suitable attachment structure or method, such as deposition manufacturing of the positive mold and first base together. The first occlusal block comprising 110a the first engagement structure may include a pocket, a keyhole, or other structure that is configured to fit over a protruding portion of the first base. The first appliance can be manufactured with thermoforming over the first positive mold of first teeth, the first base and the first occlusal block as described herein. In some embodiments, this keyed positioning system ensures that the first engagement structure is appropriately positioned within the mouth of a patient in accordance with a mandibular relocation treatment profile. The first base 136a may comprise an intrusion to receive a protrusion extending from the first engagements structure, and any type or arrangement of positioning system can be utilized to promote the proper positioning, location, and orientation of the first engagement structure. For example, a protruding structure of the first occlusal block received in the intrusion of the first based can removed prior to placing the first appliance on one or more teeth of the patient.

The second occlusal block 111b of the second engagement structure may comprise a keyed positioning system that cooperates with a second base 136b that is affixed to a positive mold of one or more mandibular teeth of a patient. In some embodiments, the keyed positioning system of the second engagement structure is different than the keyed positioning system of the first engagement structure to reduce the opportunity of locating the first and second engagement structures in the incorrect place.

Figure 7:
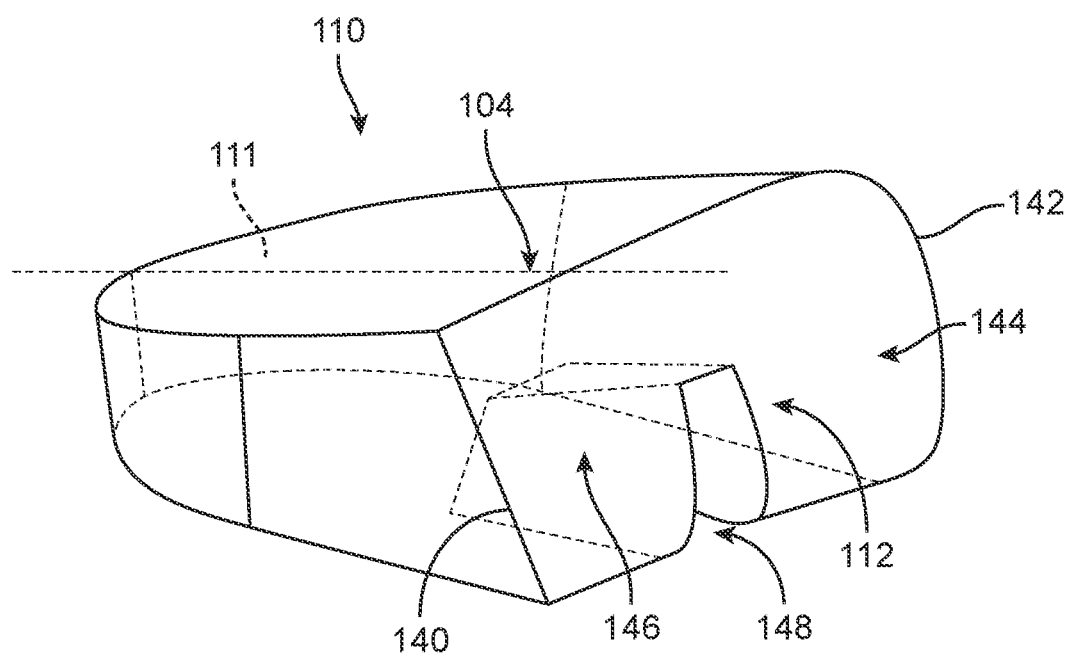
FIG. 7 shows an engagement structure having a geometry that allows it to be located within any quadrant of a dentition, in accordance with some embodiments.

FIG. 7 shows an engagement structure 110 comprising occlusal block 111 having a shape profile geometry that can be used and repeated at a plurality of locations, so as to engage a similar occlusal block at each of the plurality of locations. For example, the occlusal block 111 can be located within any quadrant of a dentition. The occlusal block 111 may comprise an engagement 112 surface that is contoured. In some embodiments, the engagement surface 112 extends to a first edge 140 the is generally flat (e.g., having a curvature of approximately zero) and to a second edge 142 that is generally convexly curved. The engagement surface 112 may define a smooth transition between the flat first edge 140 and the curved second edge 142. Thus, the engagement surface 112 defines a first portion 144 on a first side of the midline 104 having a first curvature that is different than a second curvature on a second portion 146 of the engagement surface on a second side of the midline 104.

The occlusal block may comprise a recess 148 such as a slot, channel grove or other component of the key mechanism as described herein, such as a keyway. The recess 148 can be located along the midline 104 of the occlusal block, for example.

An engagement surface 112 as shown in FIG. 7 allows a cooperating pair of occlusal block 111 comprising engagement structures 110 configured to have a substantially identical engagement surface 112. In some embodiments, the plurality of occlusal blocks comprises a substantially identical three-dimensional shape profile over the entire external surface of each of the plurality of occlusal blocks. In some embodiments, the engagement structures are used as a pair, the flat edge of a first engagement structure engages the curved edge of the second engagement structure, and likewise, the curved edge of the first engagement structure engages the flat edge of the second engagement structure.

Figure 8:
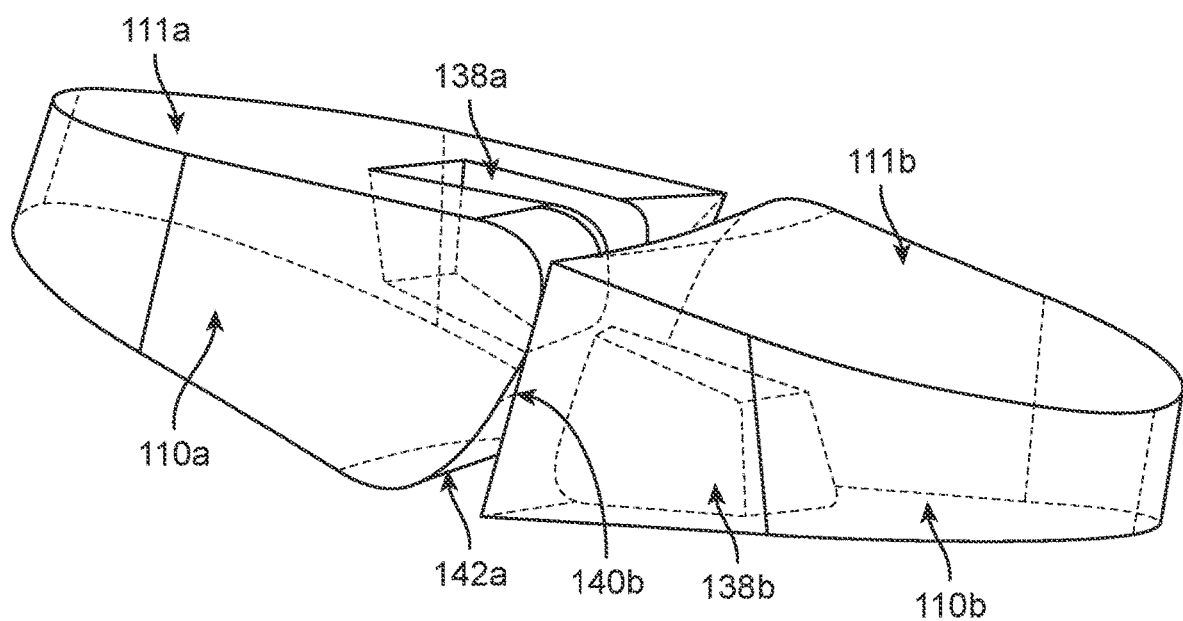
FIG. 8 shows a pair of engagement structures in an engaged position, in accordance with some embodiments.

FIG. 8 shows two cooperating engagement structures 110 as in FIG. 7 that meet at a locus of engagement, which approximates a line of engagement. As shown, the curved edge 142a of a first engagement 110a structure mates with a flat edge 140b of a second engagement structure 110b. In some instances, the engagement surfaces 112 are inclined with respect to a midline of the engagement structure. In other words, the engagement surface may not be perpendicular to the midline of the engagement structure, but is inclined at some angle, such as 10°, or 12°, or 15°, or 20° or more, or within a range defined by any two of the preceding values. In some instances, the angle of inclination is within a range from 5° to 15°. The angle of inclination may be selected such that lateral motion of the mandible relative to the maxilla is reduced by contact between the first engagement structure and the second engagement structure, for example with a pair of engagement structures located on each side of the jaw with a plurality of appliances as described herein.

In some embodiments, the overall shape of the engagement structure is selected so that a plurality of occlusal blocks comprising a plurality of engagement structures all having substantially the same shape can be used anywhere on the dentition to provide the advantages described herein. For example, a plurality of engagement structures can be manufactured on a plurality of appliances through any suitable manufacturing technique, such as a thermoforming process, molding, machining, or some other technique. The plurality of occlusal blocks comprising a plurality of engagement structures may all be substantially identical in size and shape and can be positioned on the dentition of a patient any suitable location within the mouth of the patient. For instance, engagement structures that share a substantially identical shape may be positioned in the lower left quadrant, upper left quadrant, lower right quadrant, and upper right quadrant within the mouth of a patient to provide mandible relocation. The engagement structures may be oriented and rotated as desired to provide mandible relocation forces, as described herein.

The plurality of occlusal blocks may contain a structure such as a slot, recess or keyway 138a, 138b to aid in location of each of the engagement structures. In some cases, the keyway structure extends a portion of the way through the thickness of the occlusal blocks and a portion of the engagement structures. In some embodiments, the keyway extends such that the engagement structure can be rotated and flipped around to be installed within any quadrant of the mouth of a patient while utilizing a singular geometry and three-dimensional external surface profile for the plurality of engagements structures used for mandibular relocation of a patient.

As described herein, occlusal block generally comprises a structure of material that extends generally away from the occlusal surface of one or more teeth. An engagement structure may comprise an engagement structure of an occlusal block or an oral appliance that extends away from the occlusal surface of a tooth of a patient so as to engage an opposing engagement structure. Accordingly, when appropriately positioned within the mouth of a patient, as a patient bites down, the engagement structures engage each other to generate mandibular relocation forces.

In some embodiments, the occlusal blocks comprising engagement structures are positioned on a positive mold corresponding to a dentition, and a layer of thermoformed material is placed over the occlusal blocks to form an appliance comprising engagement structures as described herein. The engagement structure may comprise the same material as the thermoformed material or a different material. In some embodiments, the thermoformed material comprises a polymeric material. The engagement structure may comprise a hardness that is similar or different than the thermoformed material, (e.g., softer or harder).

Figure 9:
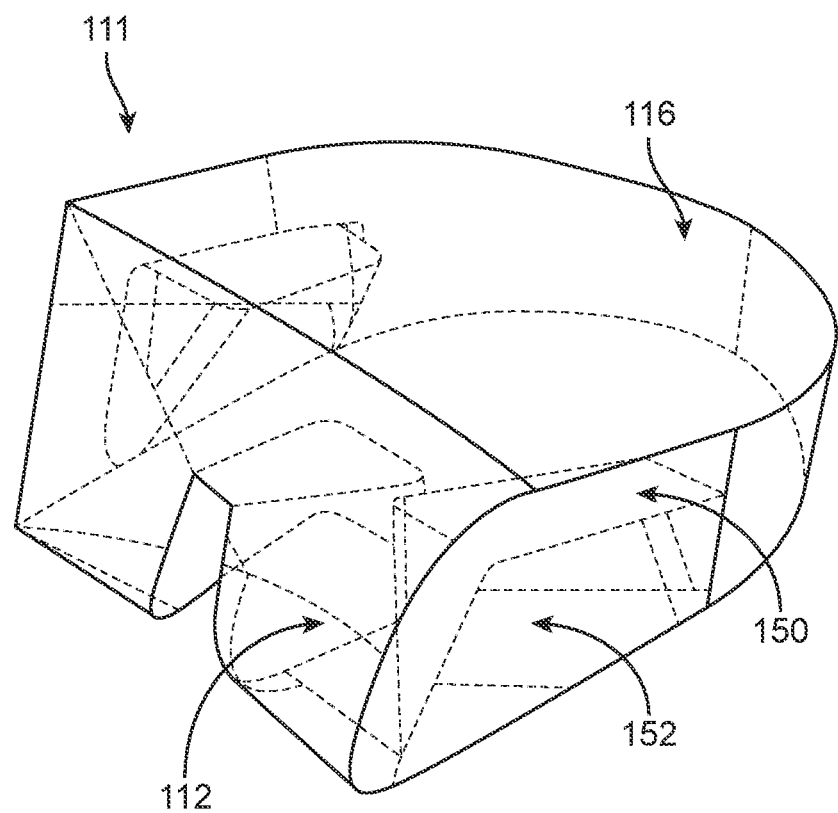
FIG. 9 shows an engagement structure with a retaining feature, in accordance with some embodiments.

FIG. 9 shows another view of the occlusal block 111 of FIGS. 7 and 8, which may comprise a retaining feature, such as undercut 152, in accordance with some embodiments. An occlusal block may comprise additional features, such as retention features so as to promote retention of the engagement structure with a corresponding appliance. As illustrated, the occlusal block 111 may comprise an engagement surface 112, an occlusal surface 116, and one or more undercuts 152 on a side surface 150. The one or more undercuts 152 may define a draft angle and be configured so that the undercut becomes greater or deeper toward the occlusal surface 116. Other retention features may be provided, such as protrusions, grooves, pockets, chamfers, draft angles, and the like to allow additional mechanical connections between the occlusal block 111 and the thermoformed material of the appliance. The one or more retention features on the occlusal block 111 are well suited for use with thermoformed appliances comprising one or more layers of polymeric material as described herein, so as to promote retention of the occlusal block 111 with the one or more layers of thermoformed material.

The undercut 152 may be formed on one or more side surfaces 150 of the engagement structure. During thermoforming, the thermoforming material may flow into the undercut 152 to provide a more secure assembly of the engagement structure within the appliance.

Figure 10:
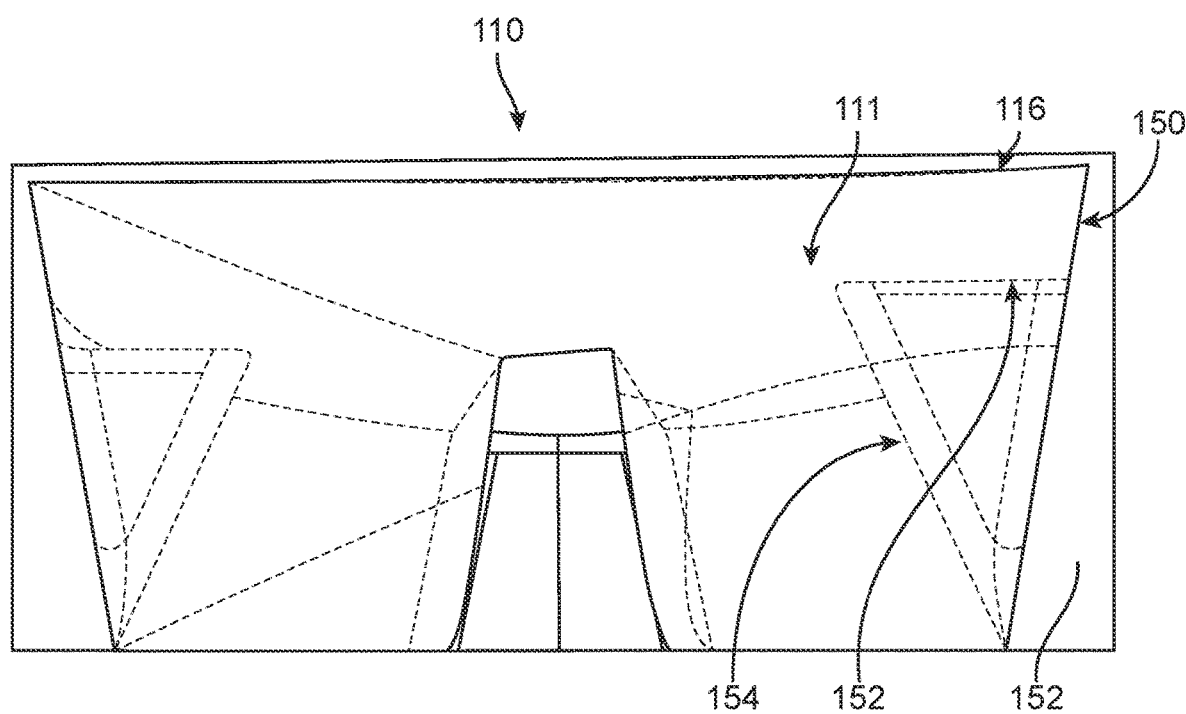
FIG. 10 shows an engagement structure with a retaining feature, in accordance with some embodiments.

FIG. 10 shows another view of an engagement structure 110 comprising an occlusal block 111 with a retaining feature, such as undercut 152, as in FIG. 9, in accordance with some embodiments. The retaining feature may comprise an undercut 152 formed by a draft 154 within the side surface 150 of the engagement structure. The angle of the draft may be on the order of or about 10° relative to the vertical axis of the engagement structure, extending perpendicular to the occlusal surface 116. Other angles are can be used, and the angle can be within a range from about 1° to about 45° to provide the benefits of the retaining feature, for example.

According to some embodiments, the occlusal block 111 is held in the thermoformed appliance 100 by the retaining feature and additional chemical or mechanical fastening means are optional. In some embodiments, the retaining feature is sufficient to maintain the engagement structure within the appliance.

Additional fastening mechanisms can be used with, or without, the retaining feature, such as any of a variety of adhesives that promote a chemical bond, a mechanical bond, or a combination. In some cases, the appliance is made by layering a thermoformed material over the engagement structure and the thermoformed material is able to flow in a softened state to fill in the retaining feature to provide a mechanical connection between the engagement structure and the appliance.

The side surface of the engagement structure may additionally have a draft angle, such that the engagement structure, as a whole, is narrower at its base and wider as it extends away from the tooth to provide additional attachment security between the engagement structure and the appliance. The draft angle may be on the order of or about 10° and may be any suitable angle within a range from about 1° to about 30°.

Figure 11:
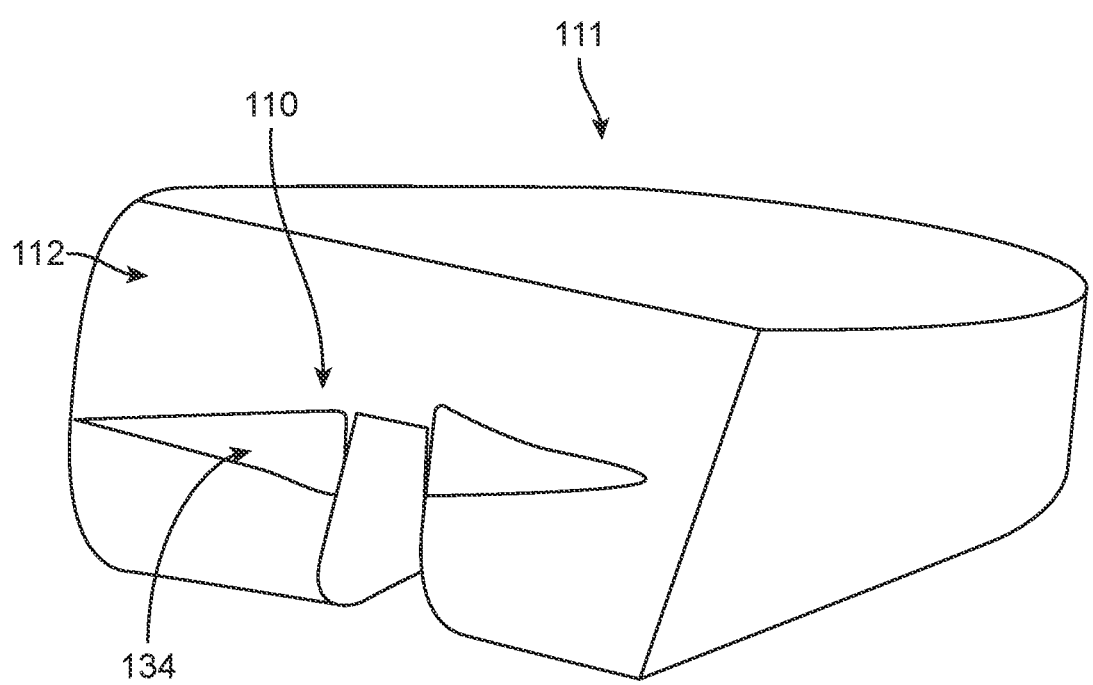
FIG. 11 shows a locus of engagement, in accordance with some embodiments.

FIG. 11 shows an engagement structure 110 of a locus of engagement 134, in accordance with some embodiments. The occlusal block 111 may comprise any of the structures of the occlusal blocks referred to in FIGS. 6 to 11. As described herein, where an engagement surface 112 of two cooperating engagement structures comprises one or more curved surfaces, the locus of engagement 134 may extend along a line. However, in some embodiments, the locus of engagement may approximate other shapes related to contact areas as described herein. As illustrated, the locus of engagement 134 may be wider near a center of the engagement surface and become thinner toward the sides of the engagement surface. The locus of engagement may comprise an external surface of an oral appliance in contact with an external surface of another appliance. Alternatively or in combination, the locus of engagement may comprise a force receiving surface of the occlusal block through which engagement force is transmitted through one or more layers of polymeric material placed over the occlusal block. In some embodiments, the locus of engagement of the occlusal block corresponds to surface contact areas of the engagement structures on exterior surfaces of the appliances in contact with each other.

In some embodiments, the locus of engagement may be substantially parallel with one or more surfaces of the engagement structure, such as the occlusal surface. However, as illustrated, in some embodiments, the locus of engagement is not parallel with the occlusal surface, and may be tilted with respect to the occlusal surface, for example as a result of varying or an asymmetric curvature of the engagement surface. Other shapes and sizes of a locus of engagement are contemplated and described herein, and the locus of engagement may follow a curved line in one, two, or three dimensions. That is, the locus of engagement may follow a curved line when viewed from the top, the front, or the side of cooperating engagement structures. Additionally, the locus of engagement may comprise an area that is less than the area of the engagement surface. For example, the locus of engagement may comprise about 10% of the area of the engagement surface. In some embodiments, the locus of engagement may comprise less than about 10%, 20%, 30%, 40%, 50%, 60%, 70%, or 80% of the area of the engagement surface. In some embodiments, the locus of engagement moves when the jaws are drawn toward each other and the mandible protruded or retracted and the contact surfaces slide with respect to each other. This movable locus of engagement can provide improved comfort for the patient because the amount of force to the mandible gradually increases as the jaws are drawn toward each other.

Figure 12:
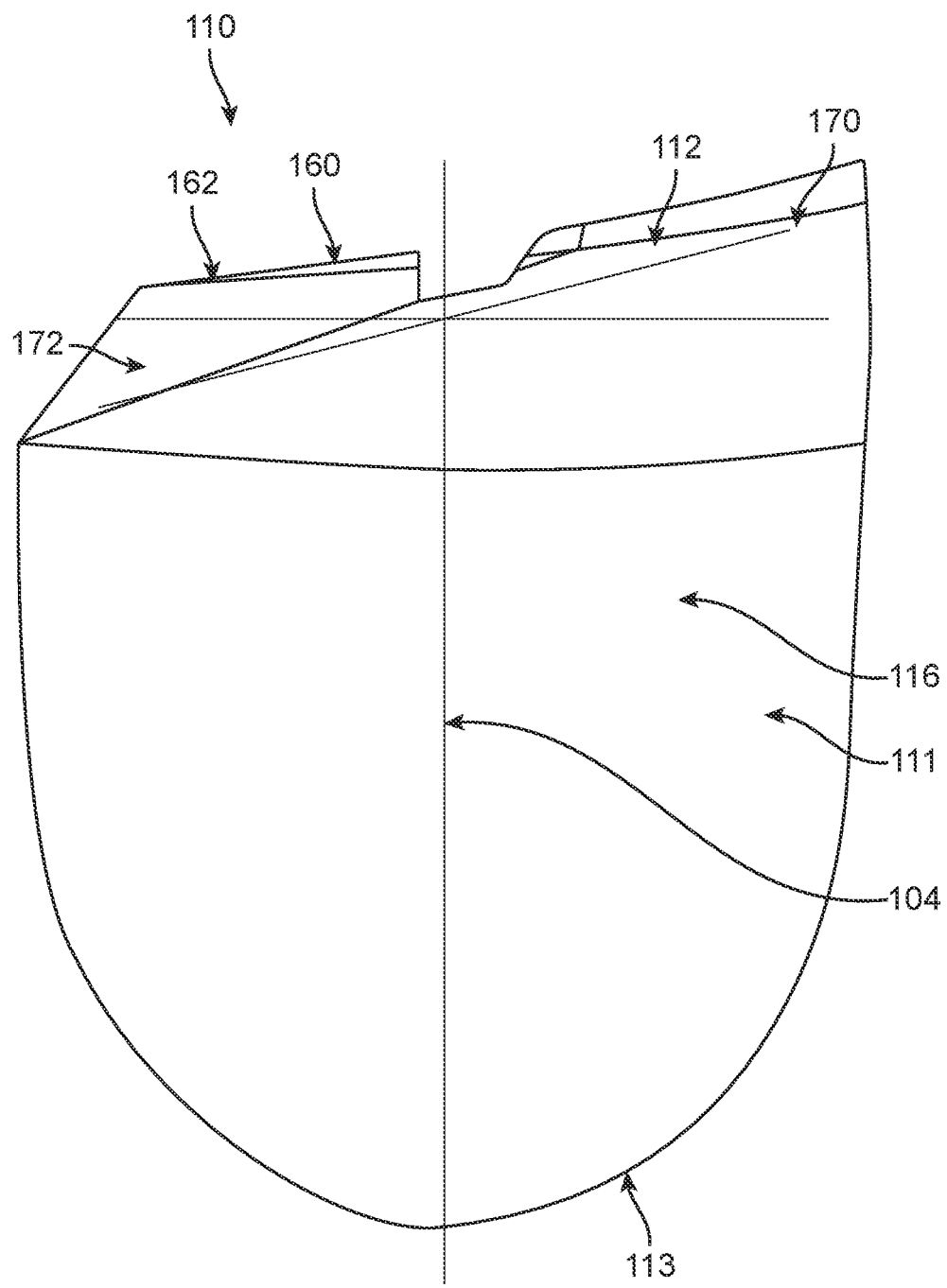
FIG. 12 shows a top view of an engagement structure, in accordance with some embodiments.

FIG. 12 shows a top view of an occlusal block 111 of an engagement structure 110 according to some embodiments. The occlusal block 111 may comprise any of the structure of the occlusal blocks of FIGS. 6 to 11. In some embodiments, the occlusal blocks of FIGS. 6 to 11 comprise the same occlusal block as shown in FIG. 12. The occlusal block 111 comprises an occlusal surface 116 and an engagement surface 112. A surface 113 opposite the engagement surface 112 may be rounded, squared, or comprise some other shape. In some embodiments, the engagement surface 112 comprises a curved profile, a flat profile or a varying curvature profile and combinations thereof. The engagement surface 112 may comprise a plurality of profiles, such as a combination of a flat profile 172, and one or more curved profiles 170. As illustrated, the engagement structure comprises a flatter profile 172 near one edge of the engagement surface, a curved profile 170 adjacent an opposite edge of the engagement surface, and a smooth grated transition between the flatter profile 172 and the curved profile 170.

As illustrated, the engagement surface 112 may be wedge-shaped when viewed from above. For example, the engagement surface may comprise an angle of inclination, 162, with respect to the midline 104. The angle of inclination, 162 or α, may comprise an angle between a lateral line extending along the engagement surface and a lateral line extending perpendicular to the midline. The angle of inclination, α, can be configured to provide mandibular relocation forces and decrease lateral movement as described herein, for example with reference to FIG. 2C. Each of the plurality of engagement structures may comprise an occlusal block as shown in FIG. 12 for example. In some embodiments, the angle of inclination, α, may be zero and the midline 104 of the engagement structure may be tangent to the dental arch of the appliance at the location of the engagement structure on the appliance.

In some instances, the engagement surface may define a curve when viewed from the top. According to some embodiments, cooperating engagement structures define engagement surfaces that are configured to cooperate to provide mandibular relocation forces as well as reducing lateral movement of the mandible. According to some embodiments, the engagement surfaces may be flat and define a surface to surface locus of engagement.

Although FIG. 2A to FIG. 12 show the occlusal blocks and associated engagement structures in isolation, one of ordinary skill in the art will readily recognize that this drawing also illustrates how these blocks can be integrated into an oral appliance such as a thermoformed appliance. For example, the first block can be placed on a positive mold of the patient's dentition and thermoformed with a material as described herein, such as a sheet of material. The thin sheet of material will thermoform over the occlusal block and positive mold of the patient's teeth. The surface contour of the thermoformed appliance will generally conform to the external surface of the positive mold of the patient's teeth with the occlusal block placed thereon. The thermoformed appliance with the occlusal blocks can be removed from the positive mold with the occlusal block attached to the appliance, and excess material removed for placement on the patient's teeth. The upper appliance can be similarly formed with a positive mold of the patient's upper teeth and the second occlusal block. In some embodiments, the thin layer of polymeric material over the occlusal blocks comprises a shape contour similar to the shape contour of the occlusal blocks, and the thin layers of material on each appliance engage each other and transmit forces similarly to the forces described with respect to the occlusal blocks as described herein.

In some embodiments, one or more of the coupled engagement surfaces may be curved, and define a locus of engagement that is substantially smaller than the engagement surface area, for example so as to allow movement of the locus of engagement. Also, the locus of engagement smaller than the engagement surface area allows the engagement surfaces to engage each other with inclination with respect to the occlusal blocks, for example.

Figure 13:
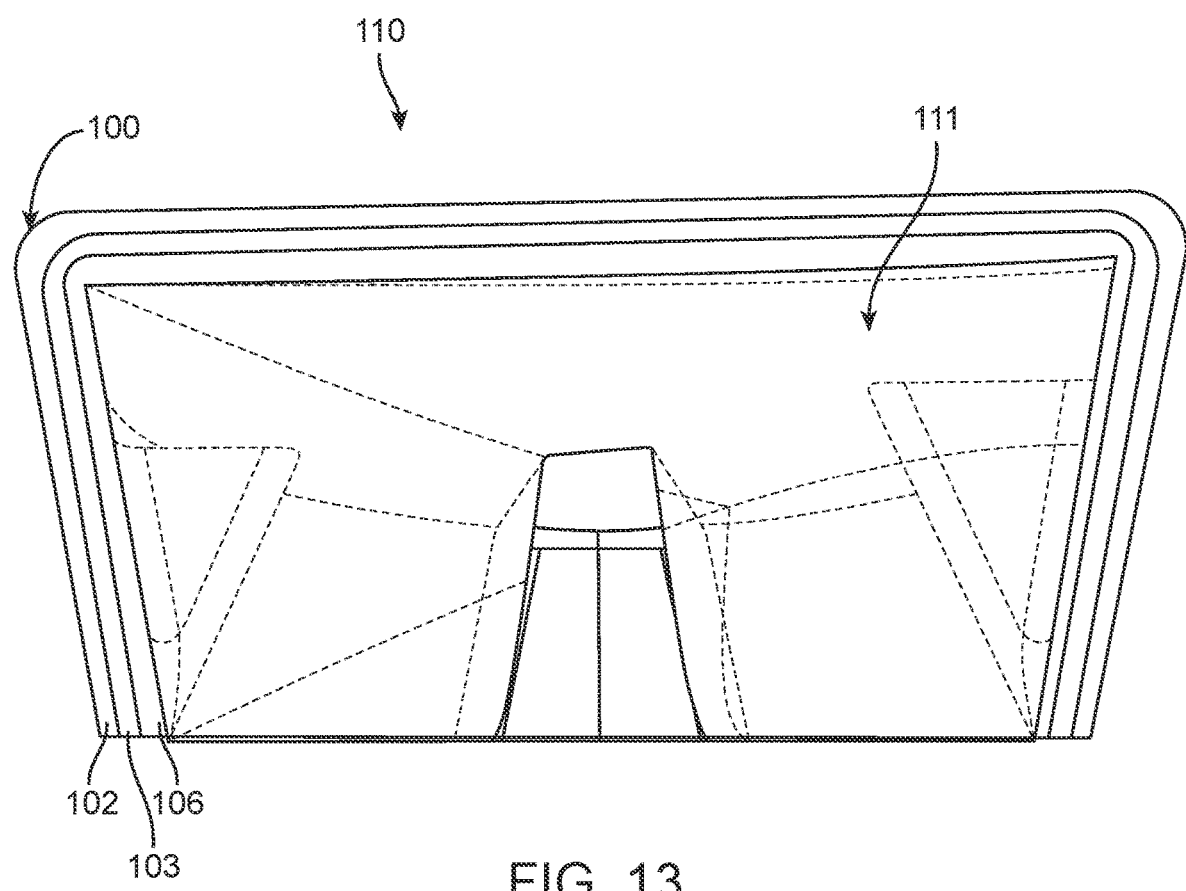
FIG. 13 shows a cross-sectional view of an appliance comprising one or more layers of thermoformed material over an occlusal block.

FIG. 13 shows a cross-sectional view of an appliance 100 comprising one or more layers 102, 103, 106 of thermoformed material over an occlusal block 111. The one or more layers 102, 103, 106 of thermoformed material may comprise a single layer of thermoformed material or a plurality of layers of thermoformed material, for example. Although one occlusal block is shown, each appliance may comprise a plurality of occlusal blocks as described herein, and a pair of appliances can be configured to engage each other to generate mandibular relocation forces as described herein. The one or more layers of thermoformed material may comprise a first layer 102, a second layer 103 and a third layer 106, in which the one or more layers are shaped to the surface profile of the underlying occlusal block. In some embodiments, the contacting surfaces of the engagement structures of the engaging appliances for mandibular relocation substantially comprise the surface shape profile of the underlying occlusal block as described herein.

In some embodiments, a first layer of thermoformed material on the first occlusal block is shaped to form an external surface of a first engagement structure of a first mandibular relocation appliance, and second layer of thermoformed material on the second occlusal block is shaped to form an external surface of a second engagement structure of a second mandibular relocation appliance. The first block and the second block can be arranged to engage each other with the first layer and the second layer therebetween. The first layer and the second layer may comprise a type of polymeric material and the first occlusal block and the second occlusal block comprise the type of polymeric material, e.g. a co-polyester or a polyurethane.

In some embodiments, the one or more layers over the occlusal block comprises a plurality of layers. For example a first plurality of layers of thermoformed materials of the first appliance can cover the first block and a second plurality of layers thermoformed material of the second appliance of the second appliance can cover the second block. The first plurality of layers may comprise a harder layer of material between two softer layers of material and the second plurality of layers may comprise the harder layer of material between the two softer layers of material. The harder layer may comprise a co-polyester and the softer layers of material may comprise thermoplastic polyurethane, for example. For example, the first layer and third layers may comprise thermoplastic polyurethane, the second layer may comprise co-polyester.

FIGS. 14-21 depict engagement structures 1410, 1510 that may share the features and benefits of the engagement structures 110 discussed herein.

Figure 14:
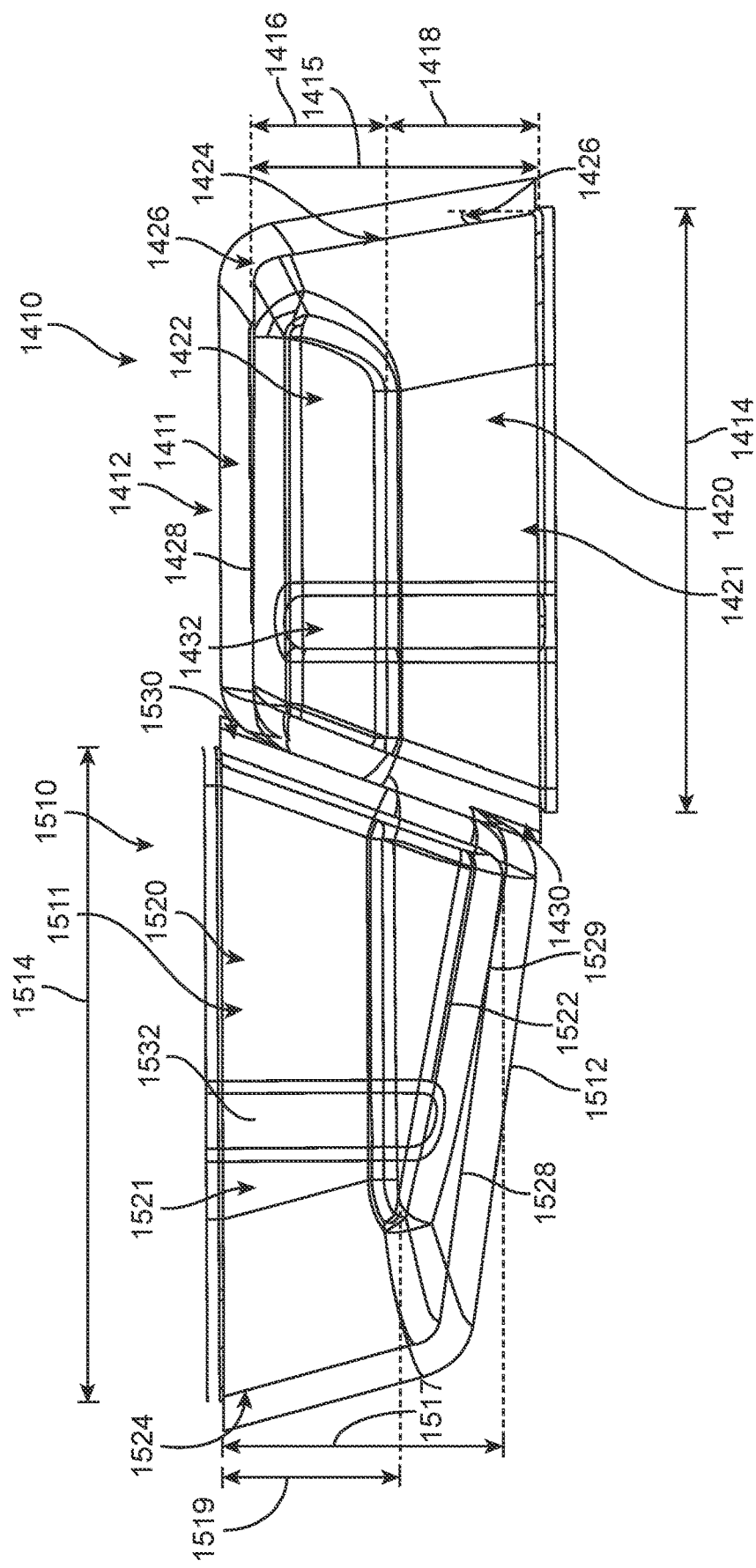
FIG. 14 shows a side view of a pair of engagement structures for repositioning a mandible and reducing lateral movement, in accordance with some embodiments.
Figure 22:
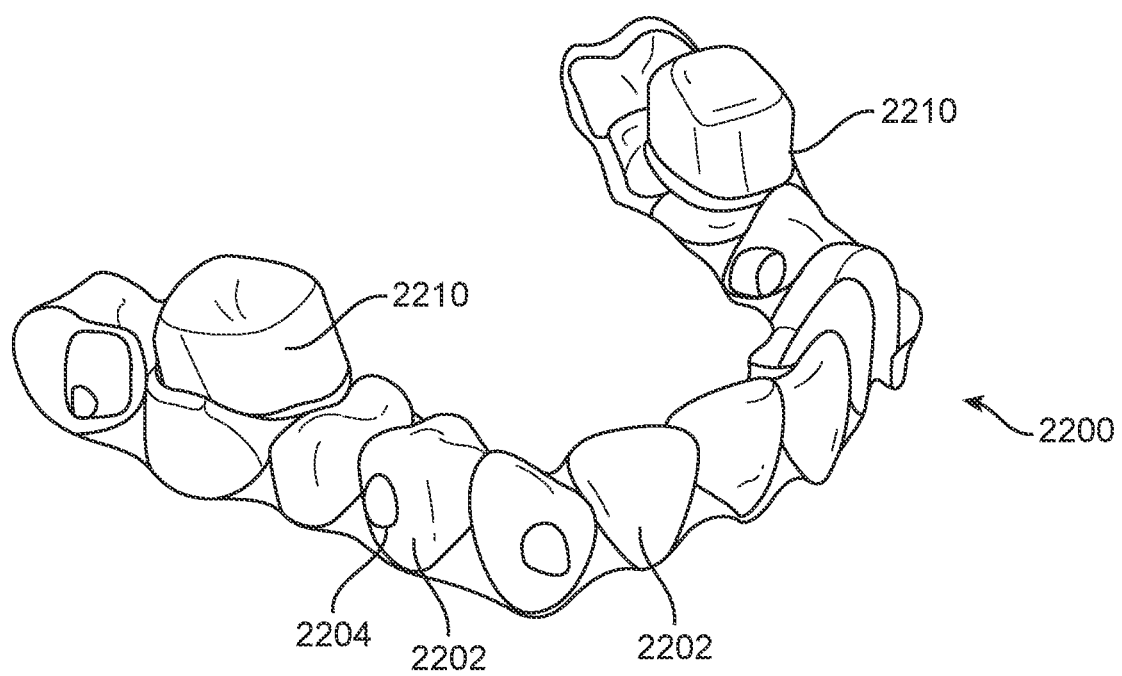
FIG. 22 shows an orthodontic aligner including engagement structures for repositioning a mandible and reducing lateral movement, in accordance with some embodiments.

FIG. 14 shows a side view of a pair of engagement structures 1410, 1510 for repositioning a mandible and reducing lateral movement. The engagement structure 1410 may include an occlusal block 1411 with an aligner portion over the occlusal block 1411. The tooth receiving cavities are omitted from FIG. 14 for clarity, however an aligner including the tooth receiving cavities and engagement structures is shown in FIG. 22. The occlusal block 1411 may include an engagement surface 1430. In the embodiment shown in FIG. 14 the engagement surface 1430 is a planar surface that faces an engagement surface of an opposing engagement structure, such as engagement structure 1510. The angle of the engagement surface 1430 with respect to the occlusal plane may match the angle of the engagement surface 1530 with respect to the occlusal plane. For example, the engagement surface 1430 may be parallel to the engagement surface 1530 when the appliances are worn by a patient. A side 1421 of the occlusal block 1411 may include an upper or first portion 1422 that is nearer the occlusal surface 1428 of the occlusal block 1411 and a lower or second portion 1420 that is further from the occlusal surface 1428 of the occlusal block 1411, as compared to the first portion 1422. The lower portion 1420 may be shaped to form an undercut, such as undercut 152 discussed above. The undercut may define a draft angle and may be configured so that the lower portion 1420 becomes wider toward the occlusal surface 1428. Other retention features may be provided, such as protrusions, grooves, pockets, chamfers, draft angles, and the like to allow additional mechanical connections between the occlusal block 1411 and the thermoformed material of the appliance 1412. The one or more retention features on the occlusal block 1411 are well suited for use with thermoformed appliances comprising one or more layers of polymeric material as described herein. The draft angles promote retention of the occlusal block 1411 with the aligner.

The undercut may be formed of the one or more side surfaces of the occlusal block. The undercut may be formed by the side surface having an angle of draft with respect to a vertical axis, such as a line perpendicular to the occlusal surface or the occlusal plane of the aligner. The draft angle may about 5 degrees relative to the vertical axis of the engagement surface, extending perpendicular to the occlusal surface. Other angles can be used, and the angle can be within a range from about 1 degree to about 45 degrees to provide the benefits of the retaining feature, for example.

In some embodiments, the draft angle may be between 1 degree at 10 degrees. More preferably between about 3 degrees and about 7 degrees.

The side surface of the aligner material may additionally have a draft angle, such that the engagement structure, as a whole, is narrower at is base and wider as it extends away from the tooth towards the upper portion 1422 in order to provide additional attachment security between the engagement structure and the appliance. The draft angle may be about 10 degrees and may be any suitable angle within a range from about 1 degree to about 45 degrees. In some embodiments, the draft angle may be about 5 degrees or between about 1 degree and about 10 degrees, more preferably between about 8 degrees and about 12 degrees or between about 3 degrees and about 7 degrees.

The upper portion 1422 may comprise a chamfer between the occlusal surface 1428 and the lower portion 1420 of the occlusal block 1411. The chamfer may be formed in or of a surface of the side 1421 of the occlusal block 1411. The chamfer may be formed of the one or more side surfaces of the other portion occlusal block. The chamfer may be formed by the side surface having an angle of chamfer with respect to a vertical axis, such as a line perpendicular to the occlusal surface. The chamfer angle may about 20 degrees relative to the vertical axis of the engagement structure, extending perpendicular to the occlusal surface or an occlusal plane of the aligner. Other angles are can be used, and the angle can be within a range from about 1 degree to about 45 degrees, for example. In some embodiments, the chamfer angle may preferably be between about 15 degrees and about 25 degrees, more between about 18 degrees and about 22 degrees.

The occlusal block 1411 may have a height 1412 that extends from a base of the occlusal block to an occlusal surface 1428 of the occlusal block 1411. The height of the occlusal block may be between 2 mm and 15 mm, more preferably between 3 mm and 12 mm, and most preferably between 5 mm and 7 mm, inclusive.

In some embodiments the occlusal block 1411 may have a height of 5 mm. In such an embodiment, the upper portion 1422 may have a height 1416 of about 2.5 mm extending from the occlusal surface 1428 to a location where the chamfer of the upper portion 1422 meets the undercut of the lower portion 1420. In such an embodiment, the lower portion may have a height 1418 of about 2.5 mm extending from a base of the occlusal block 1411 to the location where the chamfer of the upper portion 1422 meets the undercut of the lower portion 1420.

In some embodiments, the height of the upper portion and the height of the lower portion are about 50% of the overall height 1417. In some embodiments the height of the lower portion and the height of the upper portion are between 20% and 80% of the overall height 1417 of the occlusal block 1411.

The side surface of the aligner material may additionally have a chamfer angle, such that the engagement structure, as a whole, is narrower at its occlusal surface and wider as it extends away from the occlusal surface towards the lower portion. The draft angle may be about 10° and may be any suitable angle within a range from about 1° to about 45°.

The occlusal block 1411, and corresponding aligner 1412, may have an occlusal surface, such as occlusal surface 1428, that is substantially parallel to the occlusal plane of the patient's dentition or an occlusal plane of the aligner 1412. The occlusal block 1411 may include a back surface 1424 that is opposite the engagement surface 1430. The back surface may be formed at an angle 1426 with respect to the vertical axis of the engagement structure. The angle 1426 may be about 20 degrees relative to the vertical axis of the engagement structure, extending perpendicular to the occlusal surface. Other angles are can be used, and the angle can be within a range from about 0 degrees to about 45 degrees, for example. In some embodiments, the angle is between about 15 degrees and about 25 degrees, more preferably between about 18 degrees and about 22 degrees.

In some embodiments, the occlusal block 1411 may include one or more alignment structures 1432 to aid in the alignment of the occlusal block 1411 in the aligner shell 1412. The alignment structure 1432 may be an elongated keyway formed within a side 1421 of the occlusal block 1411. The alignment structure 1432 of the occlusal block may align in a direction perpendicular to the occlusal surface 1428 of the occlusal block 1411. In some embodiments, the alignment structure 1432 aligns with a corresponding alignment structure on the aligner 1412. For example, the aligner may include a key shaped to match the keyway 1432. In some embodiments, an alignment structure may be an etching or other visual indicator on the occlusal block 1411 that aligns with an etching or visual indicator on the aligner 1412 when the occlusal block is properly located within the aligner.

Similar to the engagement structure 1410, the engagement structure 1510 may include an occlusal block 1511 with an aligner over the occlusal block 1511. The engagement structure 1410 may be shaped and positioned on an aligner for placement on a lower arch of a patient, while the engagement structure 1510 is shaped and formed on an aligner for placement on an upper arch of a patient. The engagement structure 1510 may have similar features as engagement structure 1410. The occlusal block 1511 may include an engagement surface 1530. In the embodiment shown in FIG. 14 the engagement surface 1530 is a planar surface that faces an engagement surface 1430 of an opposing engagement structure, such as engagement structure 1410. The angle of the engagement surface 1530 with respect to the occlusal plane may match the angle of the engagement surface 1430 with respect to the occlusal plane. For example, the engagement surface 1430 may be parallel to the engagement surface 1530 when the appliances are worn by a patient. A side 1521 of the occlusal block 1511 may be separated into an upper or first portion 1522 that is nearer the occlusal surface 1528 of the occlusal block 1511 and a lower or second portion 1520 that is further from the occlusal surface 1528 of the occlusal block 1511, as compared to the first portion 1522. The lower portion 1520, which may be more gingivally located than the upper portion, may be shaped to form an undercut, such as undercut 152 discussed above. The undercut may define a draft angle and be configured so that the undercut lower portion becomes wider toward the occlusal surface 1528. Other retention features may be provided, such as protrusions, grooves, pockets, chamfers, draft angles, and the like to allow additional mechanical connections between the occlusal block 1511 and the thermoformed material of the appliance 1512. The one or more retention features on the occlusal block 1511 are well suited for use with thermoformed appliances comprising one or more layers of polymeric material as described herein, so as to promote retention of the occlusal block 1511 with the one or more layers of thermoformed material.

The undercut may be formed of the one or more side surfaces of the occlusal block. The undercut may be formed by the side surface having an angle of draft with respect to a vertical axis, such as a line perpendicular to the occlusal surface. The draft angle may about 5 degrees relative to the vertical axis of the engagement structure, extending perpendicular to the occlusal surface. Other angles are can be used, and the angle can be within a range from about 1 degree to about 45 degrees to provide the benefits of the retaining feature, for example. In some embodiments, the draft angle may be between about 1 degree and about 10 degrees, more preferably between about 3 degrees and about 7 degrees. The side surface of the aligner material may additionally have a draft angle, such that the engagement structure, as a whole, is narrower at its base and wider as it extends away from the tooth towards the upper portion 1522 to provide additional attachment security between the engagement structure and the appliance. The draft angle may be about 5 degrees and may be any suitable angle within a range from about 1 degrees to about 45 degrees.

The upper portion 1522 may comprise a chamfer between the occlusal surface 1428 and the lower portion 1520 of the occlusal block 1511. The chamfer may be formed in a surface of the side 1521 of the occlusal block 1511. The chamfer may be formed of the one or more side surfaces of the other portion occlusal block. The chamfer may be formed by the side surface having an angle of the chamfer with respect to a vertical axis, such as a line perpendicular to the occlusal surface. The chamfer angle may about 20 degrees relative to the vertical axis of the engagement structure, extending perpendicular to the occlusal surface. Other angles are can be used, and the angle can be within a range from about 1 degree to about 45 degrees, for example. In some embodiments, the angle is between about 15 degrees and about 25 degrees, more preferably between about 18 degrees and about 22 degrees.

The occlusal block 1511 may have a height 1517 that extends from a base of the occlusal block to an occlusal surface 1528 of the occlusal block 1511. The height of the occlusal block may be between 2 mm and 15 mm, more preferably between 3 mm and 10 mm, and most preferably between 5 mm and 7 mm, inclusive.

In some embodiments, the occlusal block 1511 may have a height of 5 mm. In such an embodiment, the upper portion 1522 may have a height of about 2.5 mm extending from the occlusal surface 1528 to a location where the chamfer of the upper portion 1522 meets the undercut of the lower portion 1520. In such an embodiment, the lower portion may have a height 1519 of about 2.5 mm extending from a base of the occlusal block 1511 to the location where the chamfer of the upper portion 1522 meets the undercut of the lower portion 1520.

In some embodiments, the height of the upper portion and the height of the lower portion are about 50% of the overall height 1515. In some embodiments the height of the lower portion and the height of the upper portion are between 25% and 75% of the overall height 1515 of the occlusal block 1511.

The side surface of the aligner material may additionally have a chamfer angle, such that the engagement structure, as a whole, is narrower at its occlusal surface and wider as it extends away from the occlusal surface towards the lower portion. The draft angle may be about 5° and may be any suitable angle within a range from about 1° to about 45°.

The occlusal block 1511, corresponding aligner 1512 may have an occlusal surface 1528 that is at an angle 1529 with respect to the occlusal plane of the patient's dentition or an occlusal plane of the aligner 1512. In some embodiments, the occlusal surface of the occlusal block 1511 is at an angle 1529 of between 3 degrees and 15 degrees with respect to the occlusal plan. Preferably the angle 1529 is between 5 degrees and 10 degrees. In some embodiments, the angle matches the Curve of Spee of the patient's dentition at the location of the engagement structure 1510. The occlusal surface may be angled with respect to the occlusal plane or to match the Curve of Spee in order to provide space between the occlusal surface of an opposing jaw. In some embodiments, the angle and/or the height of the occlusal block, such as a distal height of the block, may be provided to form a gap or clearance from the tooth surfaces of the opposing jaw. For example, the occlusal surface may have a clearance during occlusion of the patients jaws of about 1 mm, 2 mm, 3 mm, 4 mm, 5 mm, 6 mm, 7 mm, 8 mm, 9 mm, or 10 mm. In some embodiments, the clearance may be between about 1 mm and 10 mm, or between about 2 mm and about 5 mm.

The occlusal block 1511 may include a back surface 1524 that is opposite the engagement surface 1530. The back surface may be formed at an angle with respect to the vertical axis of the engagement structure. The angle may be about 10 degrees relative to the vertical axis of the engagement structure, extending perpendicular to the occlusal surface. Other angles are can be used, and the angle can be within a range from about 1 degree to about 45 degrees, for example. In some embodiments, the angle may be between about 5 degrees and about 15 degrees, more preferably between about 8 degrees and about 12 degrees.

In some embodiments, the occlusal block 1511 may include one or more alignment structures 1532 to aid in the alignment of the occlusal block 1511 in the aligner shell 1512. The alignment structure 1532 may be an elongated keyway formed within a side 1521 of the occlusal block 1511. The alignment structure 1532 of the occlusal block may align in a direction perpendicular to the occlusal surface 1528 of the occlusal block 1511. In some embodiments, the alignment structure 1532 aligns with a corresponding alignment structure on the aligner 1512. For example, the aligner may include a key shaped to match the keyway 1532. In some embodiments and alignment structure may be an etching or other visual indicator on the occlusal block 1511 that aligns with an etching or visual indicator on the aligner 1512 when the occlusal block is properly located within the aligner.

Figure 15:
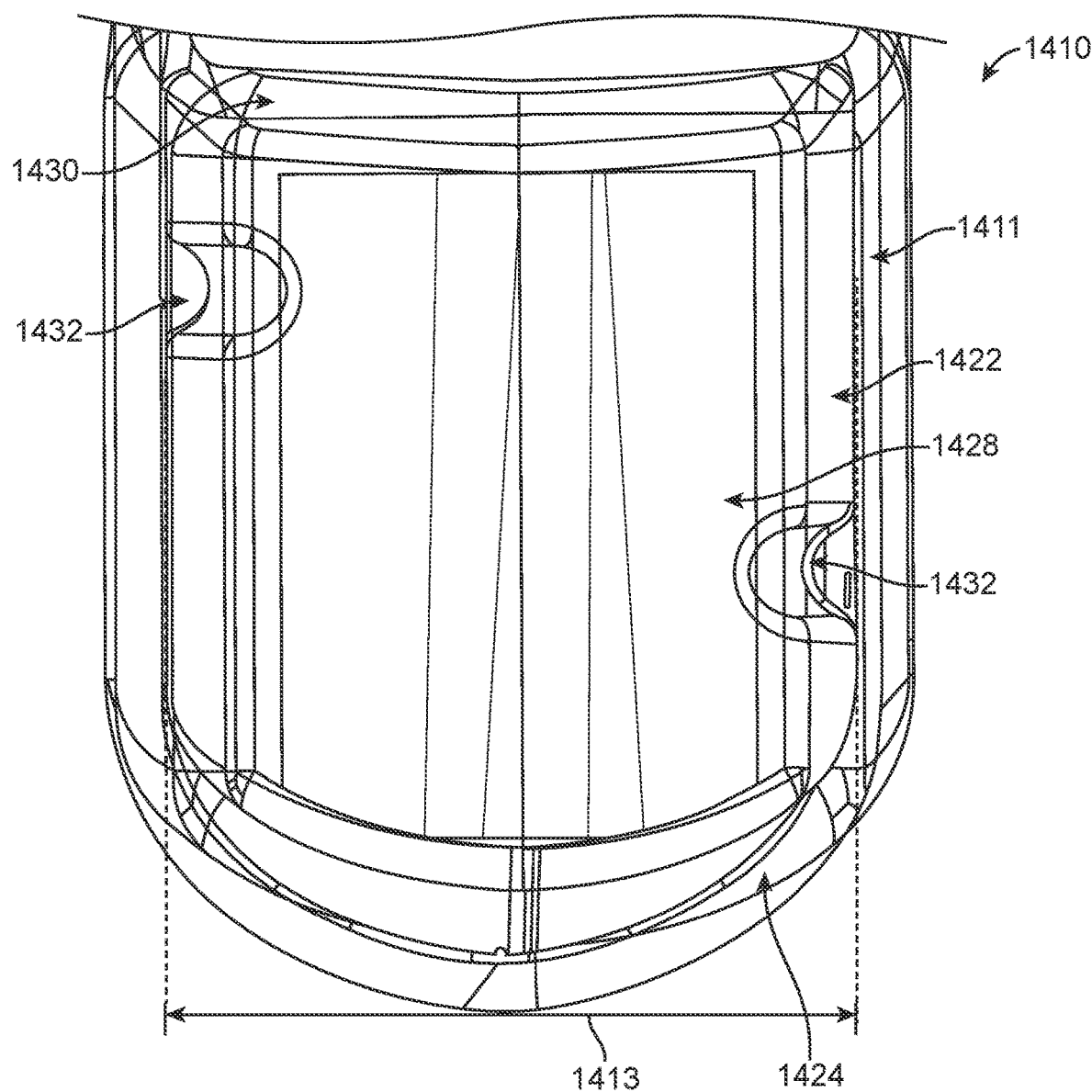
FIG. 15 shows a top view of an engagement structure for repositioning a mandible and reducing lateral movement, in accordance with some embodiments.

FIG. 15 shows a top view of an engagement structure 1410. As shown in FIG. 15 the occlusal block 1411 may include alignment structures 1432 on one or both of the buccal and lingual sides of the engagement structure. Although depicted as having a single alignment structure 1432 on each of the buccal and lingual sides of the engagement structure 1410, in some embodiments, the engagement structure may include one or more, more than 1, more than 2, or 1, 2, 3, or 4 alignment structures on each side. Although depicted as having a similar cross-sectional shape such as a circular cross-sectional shape, in some embodiments, the alignment structures may have different shapes. For example, an alignment structure on a first side of the engagement structure may have circular cross-section while an alignment structure on a second side may have an oval. Other cross-sectional shapes for alignment structures include rectangular, triangular, an asymmetrical shapes. In some embodiments a first alignment structure and associated key and keyways may be located in a more mesial position on the engagement structure while a second alignment structure is located in a more distal position on the engagement structure.

The occlusal block 1411 may have a width 1413 that extends between a most buccal portion and a most lingual portion of the occlusal block. The width may be between 5 mm and 10 mm. In some embodiments, the base and the occlusal surface of the occlusal block may also have widths. The width of the base may be the same as the width of the occlusal surface. In some embodiments the width of the occlusal surface is less than the width of the base.

Although a lower engagement structure 1410 and corresponding features are depicted in FIG. 15, similar features and dimensions are applicable to other engagement structures such as an upper engagement structure 1510.

Figure 16:
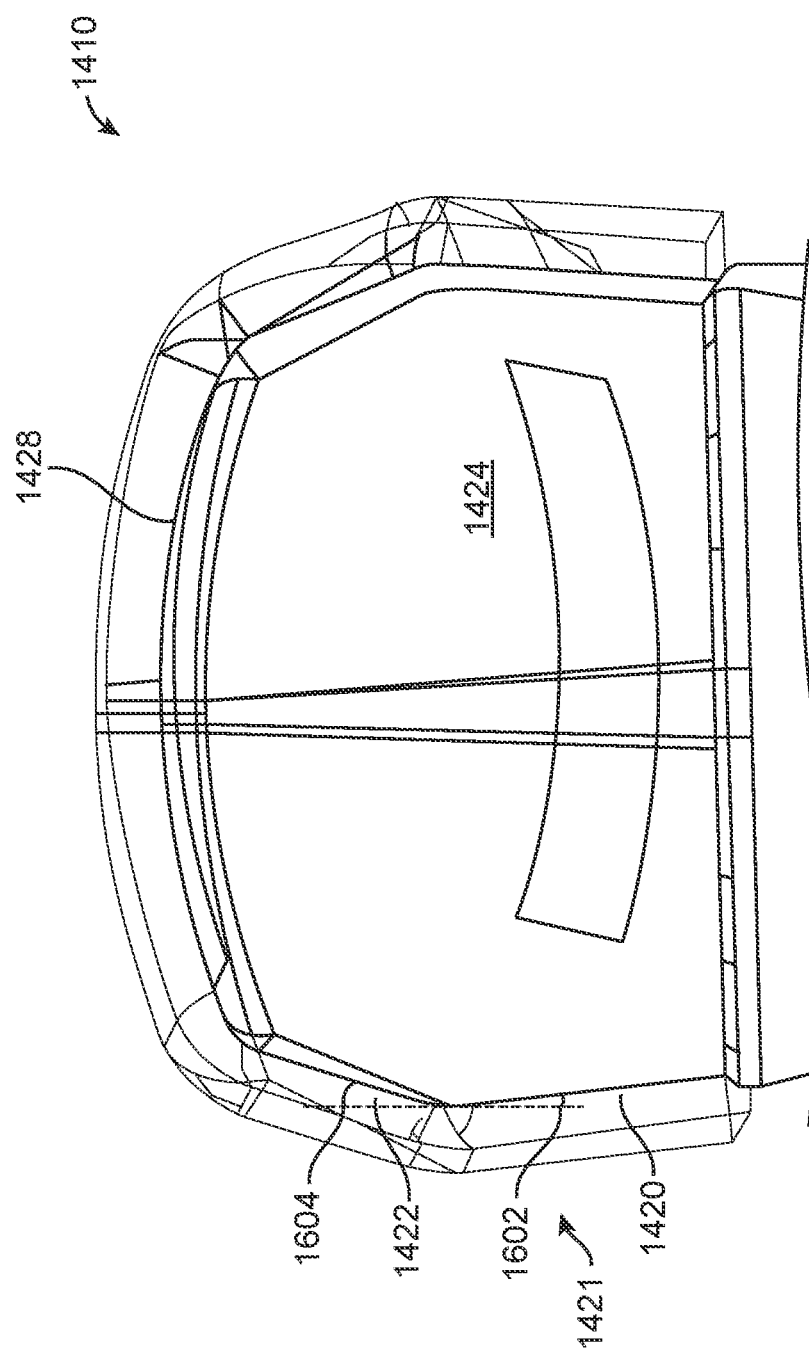
FIG. 16 shows a side of an engagement structure for repositioning a mandible and reducing lateral movement, in accordance with some embodiments

FIG. 16 shows a side of an engagement structure 1410 from a rear view looking towards the back surface 1424 of the occlusal block. A side 1421 of the occlusal block 1411 may be separated into an upper or first portion 1422 that is nearer the occlusal surface 1428 of the occlusal block 1411 and a lower or second portion 1420 that is further from the occlusal surface 1428 of the occlusal block 1411 as compared to the first portion 1422. The lower portion 1420 may be shaped to form an undercut. The undercut may define a draft angle 1602 and be configured so that the undercut becomes wider toward the occlusal surface 1428. The draft angle may about 5 degrees relative to the vertical axis of the engagement structure, extending perpendicular to the occlusal surface. Other angles are can be used, and the angle can be within a range from about 1 degree to about 45 degrees to provide the benefits of the retaining feature, for example. In some embodiments, the draft angle may be between about 1 degree and about 10 degrees, more preferably between about 3 degrees and about 7 degrees.

The side surface of the aligner material may additionally have a draft angle 1604, such that the engagement structure, as a whole, is narrower at is base and wider as it extends away from the tooth towards the upper portion 1422 to provide additional attachment security between the engagement structure and the appliance. The draft angle may be about 10 degrees and may be any suitable angle within a range from about 1 degrees to about 45 degrees. Both the lingual side and a buccal side of the occlusal block may include an undercut on their respective lower sides. In some embodiments, the lower portion does not include an under cut or a draft angle.

The upper portion 1422 may comprise a chamfer between the occlusal surface 1428 and the lower portion 1420 of the occlusal block 1411. The chamfer may be formed in a surface of the side 1421 of the occlusal block 1411. The chamfer may be formed of the one or more side surfaces of the other portion occlusal block. The chamfer may be formed by the side surface having an angle of the chamfer with respect to a vertical axis, such as a line perpendicular to the occlusal surface. The chamfer angle may about 20 degrees relative to the vertical axis of the engagement structure, extending perpendicular to the occlusal surface. Other angles are can be used, and the angle can be within a range from about 1 degree to about 45 degrees, for example both the lingual side in the buccal side of the occlusal block may include a chamfer on their respective upper sides. In some embodiments, the upper portion does not include a chamfer or a chamfer angle.

Figure 17:
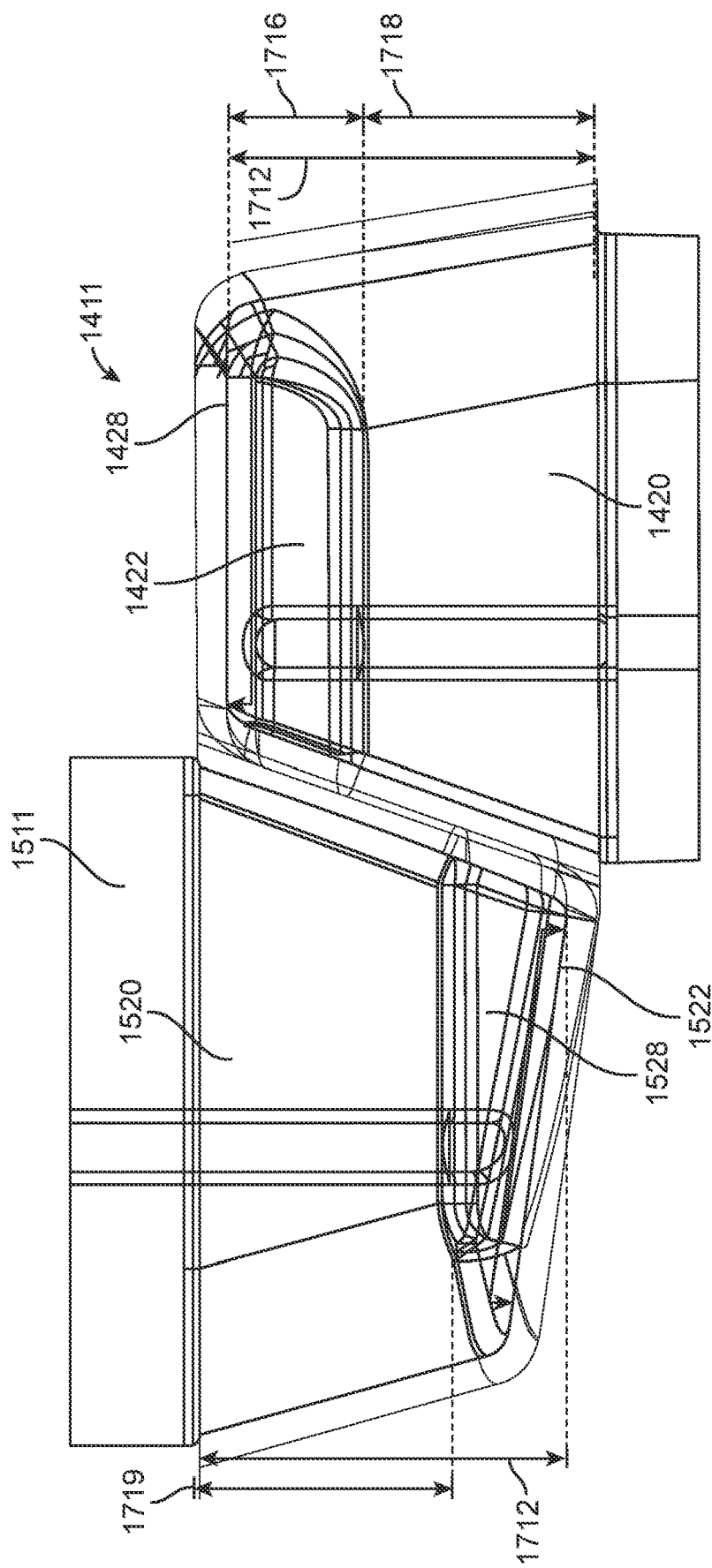
FIG. 17 shows a side view of a pair of engagement structures for repositioning a mandible and reducing lateral movement, in accordance with some embodiments.

FIG. 17 shows a side view of a pair of engagement structures. In some embodiments, the occlusal block 1411 may have a height of 7 mm. In such an embodiment, the upper portion 1422 may have a height 1716 of about 2.5 mm extending from the occlusal surface 1428 to a location where the chamfer of the upper portion 1422 meets the undercut of the lower portion 1420. In such an embodiment, the lower portion may have a height 1718 of about 4.5 mm extending from a base of the occlusal block 1411 to the location where the chamfer of the upper portion 1422 meets the undercut of the lower portion 1420.

In some embodiments, the height of the upper portion and the height of the lower portion are about 50% of the overall height 1412. In some embodiments the height of the lower portion and the height of the upper portion are between 5% and 80% of the overall height 1412 of the occlusal block 1411, more preferably between about 20% and about 40%

In some embodiments, the occlusal block 1511 may have a height 1712 of 7 mm. In such an embodiment, the upper portion 1522 may have a height of about 2.5 mm extending from the occlusal surface 1528 to a location where the chamfer of the upper portion 1522 meets the undercut of the lower portion 1520. In such an embodiment, the lower portion may have a height 1719 of about 4.5 mm extending from a base of the occlusal block 1511 to the location where the chamfer of the upper portion 1522 meets the undercut of the lower portion 1520.

In some embodiments, the height of the upper portion and the height of the lower portion are about 50% of the overall height 1515. In some embodiments the height of the lower portion and the height of the upper portion are between 5% and 80% of the overall height 1515 of the occlusal block 1511, more preferably between about 20% and about 40%

Figure 18:
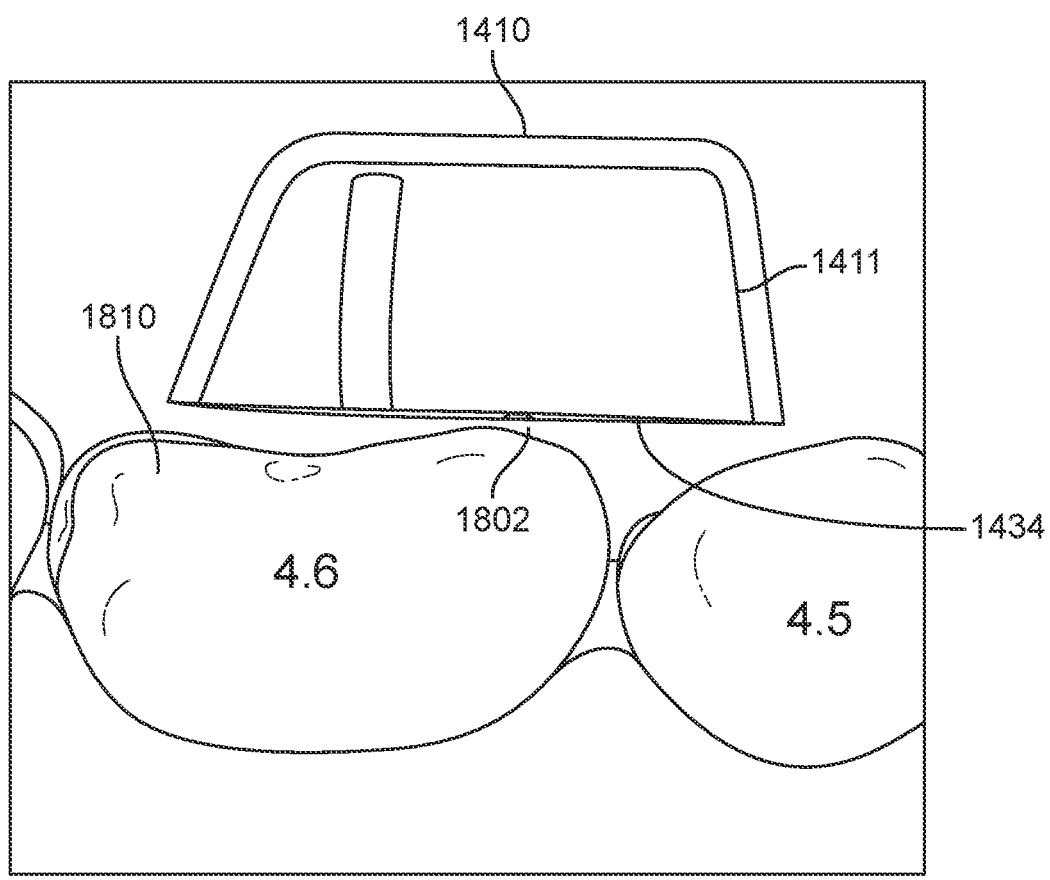
FIG. 18 shows a side view of an engagement structure for repositioning a mandible and reducing lateral movement, in accordance with some embodiments.

FIG. 18 shows a side view of an engagement structure. The location of the occlusal block 1400 of the engagement structure 1410 within the aligner may be designed such that a lower surface 1434 of the occlusal block 1411 sits at or above the most occlusal portion of the patient's dentition. For example, the occlusal block 1411 shown in FIG. 18 is above a cusp 1802 of the patient's tooth 1810. In some embodiments, the location of the occlusal block 1411 is such that the occlusal block does not interfere with the patient's dentition when the patient is not applying jaw closing forces onto the engagement structures 1410. In some embodiments, the occlusal block may be located less than 0.10 mm above the occlusal surface of the patient's tooth 1810. In some embodiments, the occlusal block may be between 0 mm and 2 mm above the occlusal surface of the patient's teeth. In some embodiments, the occlusal block may interfere with the patient's tooth. In some embodiments, the occlusal block may be located at a position such that it is less than 0.1 mm below the occlusal surface of the patient's tooth 1810.

Figure 19:
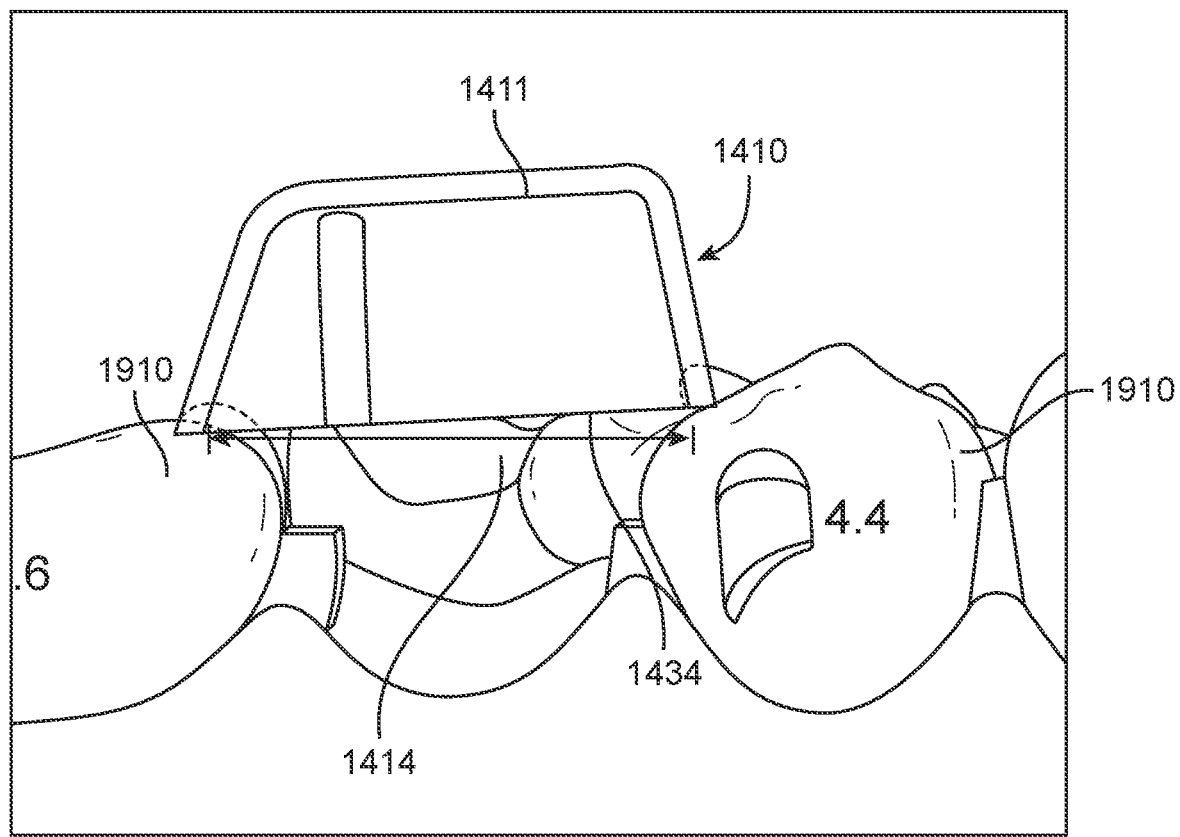
FIG. 19 shows a side view of an engagement structure for repositioning a mandible and reducing lateral movement, in accordance with some embodiments.

FIG. 19 shows a side view of an engagement structure for a lower arch.

Occlusal block 1411 may have the length 1414. The length 1414 may be such that the occlusal block spans a gap between two teeth in the patient's dental arch that may be due to a missing or erupting tooth. In this way, the patient's teeth adjacent to the gap provide support for the occlusal block 1411, such as when occlusal or repositioning forces are applied to the block. In some embodiments, the length 1414 may be patient specific such that the length 1414 of the occlusal block is between 0.5 and 6 mm longer than the width of the gap between the two nonadjacent teeth 1910. For example, the occlusal block 1411 shown in FIG. 19 has a length to span the distance between the patient's first premolar and first molar caused by a missing second premolar. In some embodiments, the occlusal block 1411 may have a length to span the distance between the patient's second premolar and second molar caused by a missing first molar. In some embodiments, the length of the occlusal block may be determined based on an average gap formed by the missing tooth. For example, for occlusal blocks on a lower arch the length may be between 8 mm and 16 mm, more preferably between, 10 mm and 14 mm. In some embodiments the length is about 12 mm.

Figure 20:
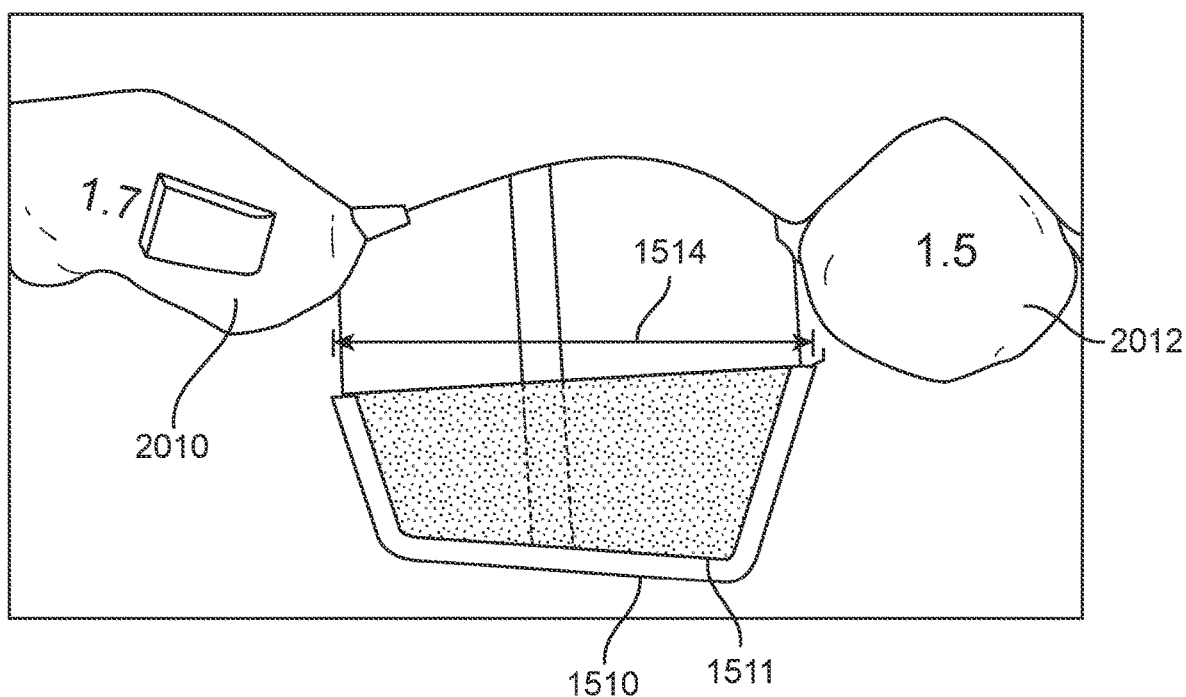
FIG. 20 shows a side view of an engagement structure for repositioning a mandible and reducing lateral movement, in accordance with some embodiments.

FIG. 20 shows a side view of an engagement structure for an upper arch. Occlusal block 1511 may have the length 1514. The length 1514 may be such that the occlusal block spans a gap between two teeth 2010, 2012 in the patient's dental arch that may be due to a missing or erupting tooth. In this way, the patient's teeth adjacent to the gap provide support for the occlusal block 1511, such as when occlusal or repositioning forces are applied to the block. In some embodiments the length 1514 may be patient specific such that the length 1514 of the occlusal block is between 0.5 and 6 mm longer than the width of the gap between the two nonadjacent teeth 1910. For example, the occlusal block 1511 shown in FIG. 20 has a length to span the distance between the patient's first premolar and first molar caused by a missing second premolar. In some embodiments the occlusal block 1511 may have a length to span the distance between the patient's second premolar and second molar caused by a missing first molar. In some embodiments, the length of the occlusal block may be determined based on an average gap formed by the missing tooth. For example, for occlusal blocks on an upper arch the length may be between 6 mm and 16 mm, more preferably between, 8 mm and 13 mm. In some embodiments the length is about 11 mm.

Figure 21:
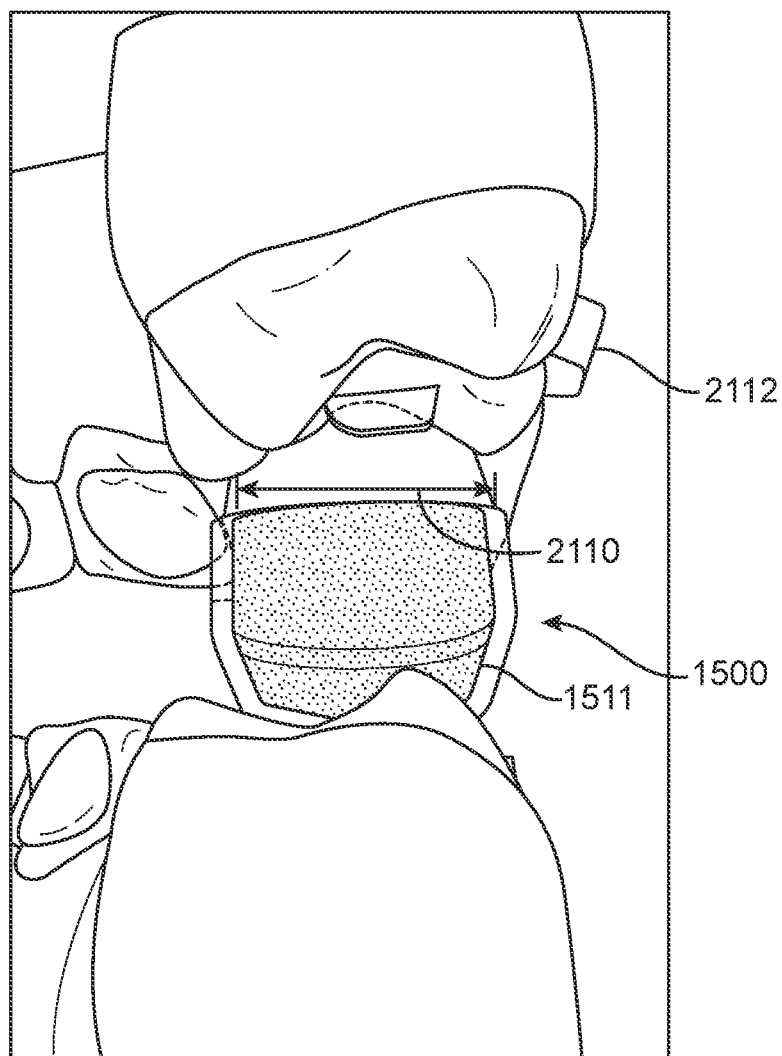
FIG. 21 shows a side of an engagement structure for repositioning a mandible and reducing lateral movement, in accordance with some embodiments.

FIG. 21 shows a view from a distal location looking mesially towards a rear surface of an engagement structure 1500. The occlusal block 1511 may have a buckle-lingual width 2110 that is less than a width of the patient's tooth over which the occlusal block is placed. The width being measured between the buckle side of the tooth and the lingual side of the tooth. Development in connection with the present disclosure has shown that an occlusal block or engagement structure with a width equal to greater than a width of the teeth over which the occlusal block is placed because interference in the use of attachments such as attachment 2112. The wide occlusal blocks act to inhibit engagement between the attachment 2112 and an orthodontic aligner. By using an occlusal block 1511 with a width 2110 that is less than a width of the respective tooth, attachments and other devices become more effective as compared to wider occlusal blocks. Occlusal blocks 1411, 1511 they have a width between 4 mm and 10 mm, more preferably between, 5 mm and 7 mm. in some embodiments the width is about 6 mm.

FIG. 22 shows an orthodontic aligner 2200 including engagement structures 2210. The orthodontic aligner 2200 may be for an upper arch or lower arch of a patient and may include two engagement structures 2210 one on each of the right and left sides of the arch of the aligner. The orthodontic aligner may be one of a plurality of orthodontic aligners provided to the patient and warn successively in order to incrementally move the patient's teeth and adjust the position of the mandible. The aligners may include tooth receiving cavities 2202 for incrementally repositioning patient's teeth. The aligner 2200 may also include one or more attachment receiving cavities 2204 for receiving an attachment placed on the patient's tooth. The engagement structures 2210 may include an occlusal block received within a cavity formed by the aligner and extending from the occlusal portion of the aligner.

In some embodiments, the occlusal blocks for a set of aligners may be selected from a set of four occlusal block shapes and sizes. For example, the occlusal blocks may be selected from a set of occlusal blocks having a height of either about 5 mm or 7 mm. In some embodiments, the occlusal blocks for a right side of the lower arch and the occlusal block for a left side of the same lower arch may have the same size and shape while occlusal blocks for the left and right side of an upper arch may have the same size and shape that is different than the size and shape of the lower occlusal blocks. In some embodiments the occlusal blocks for each of the stages of an incremental repositioning of a patient's mandible may be selected from a set of four occlusal blocks. The set of four occlusal blocks may include a lower occlusal block having a first shape and a height of 5 mm, and lower occlusal block having a second shape and a height of 7 mm, upper occlusal block having third shape and a height of 5 mm, and fourth occlusal block having fourth shape and a height of 7 mm. In some embodiments, the engagement surface of each of the four occlusal blocks may be at the same angle with respect to the occlusal plane. In some embodiments, the angle of the occlusal surface of the upper occlusal blocks may be the same.

While the occlusal blocks may comprise many suitable materials, in some embodiments, the first occlusal block and the second occlusal block each comprises a material softer than the harder layer. For example, the first occlusal block and the second occlusal block may comprise the softer material of the first layer. Work in relation to the present disclosure suggests that occlusal blocks comprising a material similar to the layer of thermoformed material in contact with the occlusal block can improve bonding of the occlusal block to the appliance. For example, the first of the one or more layer may comprise polyurethane and the occlusal block may comprise polyurethane.

The occlusal blocks disclosed herein can be manufactured in many ways, for example with computer numeric control (CNC) machining, molding such as injection molding and additive manufacturing. The presently disclosed engagement structures and appliances are well suited for additive manufacturing. In some embodiments, the engagement structure and appliance can be directly manufactured with additive manufacturing as a single integrated component. For example, the shaped engagement structures as described herein can be directly fabricated with the appliance to form an integrated appliance, in which the occlusal blocks are directly fabricated with the polymer shell appliance as a single part, as will be appreciated by one of ordinary skill in the art.

Examples of suitable harder and softer materials suitable for combination in accordance with embodiments of the present disclosure are described in U.S. Pat. No. 9,655,693, entitled "Multilayer dental appliances and related systems", issued May 23, 2017, the entire disclosure of which is incorporated herein by reference. The occlusal blocks may comprise any material disclosed herein, for example a hard material or a soft material and may comprise a material similar to the material of the appliance or a material different from the material of the appliance.

In some embodiments, the hard polymer layer can be thicker than either of the soft polymer layers. The soft polymer layers can have the same or different thicknesses. For example, the hard polymer layer can range from a thickness of about 550 micrometers ("microns") to about 750 microns. The soft polymer layers can range from a thickness of about 25 microns to about 100 microns. Multilayer sheets used for making appliances having a hard polymer layer disposed between two soft polymer layers can range from a thickness of about 600 microns to about 1000 microns. In some embodiments, the thicknesses of the various layers can be tailored for a particular stage of treatment for the patient.

Suitable polymeric materials for the hard polymer layer can include a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof (e.g., a blend of at least two of the listed hard polymeric materials). In some embodiments, the hard polymer layer of the appliances can include polymeric materials, such as a polycarbonate, a co-polyester, a polyester, and a thermoplastic polyurethane. In some embodiments, the hard layer can be composed of multiple hard layers, e.g., two or three hard polymer layers co-extruded to form one hard layer.

The hard polymer layer of the appliances of the present invention can have a variety of physical properties that can, e.g., improve treatment options for a practitioner. For example, physical properties such as tensile strength, elongation at yield, elongation at break, tensile modulus, flexural modulus, stress relaxation over time, and light transmission can each be specifically tailored for a particular application. In some embodiments, the hard polymer layer of the appliances can have a physical property of at least one of a tensile strength at yield of between about 4000 pounds per square inch (psi) and 6500 psi, an elongation at yield of greater than about 4%, an elongation at break of greater than about 70%, a tensile modulus of greater than about 150,000 psi, a flexural modulus greater than about 150,000 psi, a stress relaxation at 24 hours testing in a wet environment (e.g., between about 90%-100% relative humidity) is greater than 10%, and a light transmission between 400 nm and 800 nm of greater than about 75%.

Suitable polymeric materials for the soft polymer layers of the appliance can include a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or a combination thereof (e.g., a blend of at least two of the listed soft polymeric materials). The soft polymer layers can be the same material or a different material. In certain embodiments, the first soft polymer layer and the second soft polymer layer are the same polymeric material.

The soft polymer layers of the appliances can have a variety of physical properties. For example, physical properties such as hardness, ultimate tensile strength, elongation at break, tensile modulus, compression set, flexural modulus, and light transmission can each be specifically tailored for a particular application. In some embodiments, the soft polymer layers of the appliances can independently have a physical property of at least one of a hardness within a range from about 60 A to about 85 D, an ultimate tensile strength of greater than about 5000 psi, an elongation at break of greater than about 200%, a compression set at about 70.degree. C. of greater than 40% after 24 hours, a flexural modulus of greater than about 35,000 psi, and a light transmission between 400 nm and 800 nm of greater than about 75%.

As described herein, the layers of the appliances can include a hard polymer layer disposed between two soft polymer layers. In one embodiment, the multilayer appliances can include a hard polymer layer of one type of material (e.g., a co-polyester), and two soft polymer layers of other types of material that can be the same or different (e.g., two soft polymer layers of thermoplastic polyurethane elastomer). In some embodiments, the multilayer appliances can also include a hard polymer layer of at least two layers of polymer material. For example, the hard polymer layer can include several polymer layers laminated together to form the hard polymer layer. The laminated hard polymer layer can include at least two layers of any combination of the following polymer materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and a polytrimethylene terephthalate. Similarly, in some embodiments, the multilayer appliances can include a soft polymer layer of at least two layers of polymer material. For example, the soft polymer layers can include a layer of several polymer layers, laminated together. The laminated soft polymer layers can include at least two layers of any combination of the following polymer materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and a thermoplastic polyamide elastomer.

The tooth positioning appliances can be fabricated using a variety of methods. For example, methods for making the appliances can include thermoforming a multilayer sheet into an aligner by heating the sheet and then molding the sheet to a particular configuration. Exemplary methods for fabricating the appliances, including those utilized in the Invisalign™. System, are described in numerous patents and patent applications assigned to Align Technology, Inc. including, for example, in U.S. Pat. No. 9,108,338, entitled "Methods and systems thermoforming an object," issued on Aug. 18, 2015, as well as on the company's website, which is accessible on the World Wide Web (see, e.g., the url "invisalign.com").

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of" Finally, for ease of use, the terms "including" and "having" (and their derivatives), as used in the specification and claims, are interchangeable with and shall have the same meaning as the word "comprising".

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination, unless indicated otherwise.

As used herein, characters such as numerals refer to like elements.

The present disclosure includes the following numbered clauses.

Clause 1. A plurality of occlusal blocks for a mandibular relocation, comprising: a first occlusal block comprising a first surface; and a second occlusal block comprising a second surface to engage the first surface; wherein the first surface and the second surface are shaped to engage each other with a curvature difference.

Clause 2. The plurality of occlusal blocks of clause 1, wherein the first surface and the second surface comprise similar shape profiles oriented in opposing directions.

Clause 3. The plurality of occlusal blocks of clause 1, wherein the first surface and the second surface are shaped to engage each other along an engagement line.

Clause 4. The plurality of occlusal blocks of clause 3, wherein the first surface and the second surface are shaped to engage each other with the curvature difference along a substantially straight line.

Clause 5. The plurality of occlusal blocks of clause 3, wherein the first surface and the second surface are shaped to engage each other at a locus of engagement, the locus of engagement extending along the line.

Clause 6. The plurality of occlusal blocks of clause 1, wherein the first occlusal block comprises a first midline and the first surface comprises a first portion on a first side of the midline and a second portion on a second side of a midline, the first portion comprising a curvature different from the second portion.

Clause 7. The plurality of occlusal blocks of clause 6, wherein the second occlusal block comprises a second midline and the second surface comprises a first portion on a first side of the second midline and a second portion on a second side of the second midline, the first portion comprising a curvature different from the second portion.

Clause 8. The plurality of occlusal blocks of clause 7, wherein the first portion of the first surface comprises a curvature corresponding to a curvature of the second portion of the second surface and a curvature of the second portion of the first surface comprises a curvature corresponding to a curvature of the first portion of the second surface.

Clause 9. The plurality of occlusal blocks of clause 8, wherein each of the first portion and the second portion of the first surface and the first portion and the second portion of the second surface comprise convex surfaces.

Clause 10. The plurality of occlusal blocks of clause 8, wherein the curvature of the first portion of the first surface matches the curvature of the second portion of the second surface and the curvature of the second portion of the first surface matches the curvature of the first portion of the second surface.

Clause 11. The plurality of occlusal blocks of clause 8, wherein one or more of the first portion or the second portion of the first surface comprises a curvature of zero and wherein one or more of the first portion or the second portion of the second surface comprises a curvature of zero.

Clause 12. The plurality of occlusal blocks of clause 1, wherein a first 3D shape profile of the first surface and a second 3D shape profile of the second surface correspond to each other and optionally wherein the first 3D shape profile matches the second 3D shape profile.

Clause 13. The plurality of occlusal blocks of clause 1, wherein the first occlusal block and the second occlusal block correspond to replicas of each other.

Clause 14. The plurality of occlusal blocks of clause 13, wherein the first occlusal block comprises a first 3D exterior surface shape profile and the second occlusal block comprises a second 3D exterior surface shape profile and wherein the first 3D exterior surface shape profile matches the second 3D exterior surface shape profile to within 90% and optionally wherein the first occlusal block comprises a first volume and the second occlusal block comprises a second volume matching the first volume to within 90%.

Clause 15. The plurality of occlusal blocks of clause 1, comprising a first layer of thermoformed material on the first occlusal block to shape a first engagement structure of a first mandibular relocation appliance and second layer of thermoformed material on the second occlusal block to shape a second engagement structure of a second mandibular relocation appliance.

Clause 16. The plurality of occlusal blocks of clause 15, wherein the first block and the second block are arranged to engage each other with the first layer and the second layer therebetween.

Clause 17. The plurality of occlusal blocks of clause 16, wherein the first layer and the second layer comprise a type of polymeric material and the first occlusal block and the second occlusal block comprise the type of polymeric material.

Clause 18. The plurality of occlusal blocks of clause 15, comprising a first plurality of layers of thermoformed materials of the first appliance on the first block and a second plurality of layers thermoformed material of the second appliance of the second appliance on the second block.

Clause 19. The plurality of occlusal blocks of clause 18, wherein the first plurality of layers comprises a harder layer of material between two softer layers of material and the second plurality of layers comprises the harder layer of material between the two softer layers of material, and optionally wherein the harder layer comprises a co-polyester and the softer layers of material comprise thermoplastic polyurethane.

Clause 20. The plurality of occlusal blocks of clause 19, wherein the first occlusal block and the second occlusal block each comprises a material softer than the harder layer.

Clause 21. An apparatus for a mandibular relocation, comprising: a first appliance comprising a first engagement structure, the first engagement structure comprising a first engagement surface facing generally anteriorly and inclined with respect to a first midline of the first engagement structure; and a second appliance comprising a second engagement structure, the second engagement structure comprising a second engagement surface facing generally posteriorly and inclined with respect to a midline of the second engagement structure; wherein one or more of the first engagement surface or the second engagement surface is curved to create an engagement line in a lingual-buccal direction with engagement between the first engagement surface and the second engagement surface.

Clause 22. The apparatus of clause 21, further comprising the plurality of occlusal blocks of any one of clauses 1 to 20.

Clause 23. An apparatus for mandibular relocation comprising: a first appliance comprising, a first plurality of a teeth receiving cavities, a first engagement structure comprising a first engagement surface, and a second engagement structure comprising a second engagement surface; and a second appliance comprising, a second plurality of teeth receiving cavities, a third engagement structure comprising a third engagement surface to engage the first engagement surface, and a fourth engagement structure comprising a fourth engagement surface to engage the second engagement surface; wherein the first and second engagement surfaces are inclined with respect to the third and fourth engagement surfaces, respectively, to generate mandibular relocation forces and limit a lateral movement of the mandible.

Clause 24. The apparatus of clause 23, further comprising the plurality of occlusal blocks of any one of clauses 1 to 20, and wherein the first engagement structure comprises the first occlusal block and the third engagement structure comprises the second occlusal block.

Clause 25. The apparatus of clause 24, further comprising a third occlusal block corresponding to the first occlusal block and a fourth occlusal block corresponding the second occlusal block and wherein the second engagement structure comprises the third occlusal block and the fourth engagement structure comprises the fourth occlusal block.

Clause 26. The apparatus of clause 23, wherein the first engagement surface is inclined relative to a midline of the first engagement structure and the second engagement surface is opposingly inclined relative to a midline of the second engagement structure to limit the lateral movement of the mandible and reposition the mandible.

Clause 27. The apparatus of clause 23, wherein the third engagement surface is inclined relative to a midline of the third engagement structure and the fourth engagement surface is opposingly inclined relative to a midline of the fourth engagement structure to limit lateral movement of the mandible and reposition the mandible.

Clause 28. The apparatus of clause 23, wherein the first and second engagement surfaces face generally anteriorly and wherein the third and fourth engagement surfaces face generally posteriorly to engage the first and second engagement surfaces to generate the mandibular relocation forces.

Clause 29. The apparatus of clause 23, wherein the first and second engagement surfaces face generally posteriorly and wherein the third and fourth engagement surfaces face generally anteriorly to engage the first and second engagement surfaces to generate the mandibular relocation forces.

Clause 30. The apparatus of clause 23, wherein one or more of the first engagement structure, the second engagement structure, the third engagement structure or the fourth engagement structure extends from an occlusal surface of one or more of the first appliance or the second appliance and optionally wherein the one or more of the first engagement surface, the second engagement surface, the third engagement surface or the fourth engagement surface is located between occlusal surfaces of the first appliance and the second appliance.

Clause 31. The apparatus of clause 23, wherein one or more of the first engagement surface or the third engagement surface comprises a curved surface to create a first locus of engagement and wherein one or more of the second engagement surface or the fourth engagement surface comprises a curved surface to create a second locus of engagement.

Clause 32. The apparatus of clause 31, wherein the curved surface provides engagement between the first engagement surface and the third engagement surface to accommodate a curve of Spee of a mouth and optionally wherein a location of the locus of engagement changes with subsequent appliances in response to changes of the curve of Spee.

Clause 33. The apparatus of clause 31, wherein the first engagement surface and the third engagement surface are shaped to contact each other at the first locus of engagement and provide a sliding locus of engagement between the first engagement surface and the third engagement surface to generate the mandibular relocation forces and limit lateral movement.

Clause 34. The apparatus of clause 31, wherein the second engagement surface and the fourth engagement surface are shaped to contact each other at the second locus of engagement and provide sliding locus of engagement between the second engagement surface and the fourth engagement surface to generate the mandibular relocation forces and limit lateral movement.

Clause 35. The apparatus of clause 31, wherein the first locus engagement comprises a first engagement area that is less than one or more of a first surface area of the first engagement surface or a second surface area of the second engagement surface and wherein the second locus engagement comprises a second engagement area that is less than one or more of a third surface area of the third engagement surface or a fourth surface area of the fourth engagement surface.

Clause 36. The apparatus of clause 35, wherein the first engagement area comprises a contact area between the first engagement surface and the second engagement surface and the second engagement area comprises a contact area between the third engagement surface and the fourth engagement surface.

Clause 37. The apparatus of clause 23, wherein the mandibular relocation forces comprise mandibular advancement forces.

Clause 38. The apparatus of clause 23, wherein the mandibular relocation forces comprise mandibular retraction forces.

Clause 39. The apparatus of clause any one of the preceding clauses, wherein one or more of a first appliance or a second appliance comprises a polymeric shell appliance.

Clause 40. A method, the method comprising using the plurality of occlusal blocks or the appliance of any one of the preceding clauses.

Clause 41. A plurality of occlusal blocks for a mandibular relocation, comprising: a first occlusal block comprising a first engagement surface and a first side surface; a first keyway formed in the first side surface of the first occlusal block; a second occlusal block comprising a second engagement surface to engage the first engagement surface and a second side surface; and a second keyway formed in the second side surface of the first occlusal block.

Clause 42. The plurality of occlusal blocks of clause 41, wherein the first side surface has a lower portion and an upper portion.

Clause 43. The plurality of occlusal blocks of clause 42, wherein the lower portion extends from a base towards an occlusal surface.

Clause 44. The plurality of occlusal blocks of clause 43, wherein the upper portion extends from the occlusal surface towards the base.

Clause 45. The plurality of occlusal blocks of clause 44, wherein the upper portion meets the lower portion along a mesial-distal line between the occlusal surface and the base.

Clause 46. The plurality of occlusal blocks of clause 45, the first side surface of the lower portion extends from the base towards the upper portion at a draft angle with respect to a line perpendicular to the occlusal plane.

Clause 47. The plurality of occlusal blocks of clause 46, wherein the first side surface is a buccal side surface and the first occlusal block includes a lingual side surface, opposite the buccal side surface, the lingual side surface extending from the base at the draft angle.

Clause 48. The plurality of occlusal blocks of clause 47, wherein the draft angle is between 1 degree and 10 degrees.

Clause 49. The plurality of occlusal blocks of clause 47, wherein the draft angle is about 5 degrees.

Clause 50. The plurality of occlusal blocks of clause 45, the first side surface of the upper portion defines a chamfer that extends from the occlusal surface towards the lower portion at an angle with respect to a line perpendicular to the occlusal plane.

Clause 51. The plurality of occlusal blocks of clause 46, wherein the first side surface is a buccal side surface and the first occlusal block includes a lingual side surface, opposite the buccal side surface, the upper portion of the lingual side surface defining a chamfer extending from the occlusal surface at the angle.

Clause 5.2 The plurality of occlusal blocks of clause 50, wherein the angle is between 15 degrees and 25 degrees.

Clause 53. The plurality of occlusal blocks of clause 50, wherein the angle is about 20 degrees.

Clause 54. The plurality of occlusal blocks of clause 41, wherein the occlusal blocks have a height of about 5 mm.

Clause 55. The plurality of occlusal blocks of clause 41, wherein the occlusal blocks have a height of about 7 mm.

Clause 56. The plurality of occlusal blocks of clause 41, wherein the first occlusal block includes an occlusal surface, the occlusal surface being parallel to an occlusal plane of the dentition of the patient.

Clause 57. The plurality of occlusal blocks of clause 41, wherein the second occlusal block includes an occlusal surface, the occlusal surface being at an angle with respect to the occlusal plane, the angle being between about 15 degrees and about 25 degrees.

Clause 58. The plurality of occlusal blocks of clause 57, wherein the angle being between about 3 degrees and about 15 degrees.

Clause 59. The plurality of occlusal blocks of clause 57, wherein being between about 5 degrees and about 10 degrees.

Clause 60. The plurality of occlusal blocks of clause 57, wherein the angle is corresponds to the angle of the curve of Spee at the location of the occlusal block.

Clause 61. The plurality of occlusal blocks of clause 41, wherein a base of the occlusal block has a length, the length extending form a mesial most edge to a distal most edge of the base, the length being between 8 mm and 16 mm.

Clause 62. The plurality of occlusal blocks of clause 61, wherein the length is between 10 mm and 14 mm.

Clause 63. The plurality of occlusal blocks of clause 61, wherein the length is about 14 mm.

Clause 64. The plurality of occlusal blocks of clause 41, wherein a base of the occlusal block has a width, the width extending form a buccal most edge to a lingual most edge of the base, the width being between 4 mm and 10 mm.

Clause 65. The plurality of occlusal blocks of clause 61, wherein the width is between 5 mm and 7 mm.

Clause 66. The plurality of occlusal blocks of clause 61, wherein the width is about 6 mm.

Clause 67. A system comprising: a plurality of orthodontic aligners, each of the plurality of orthodontic aligners having: tooth receiving cavities for incrementally repositioning a patient's teeth from an initial position towards a final position; and engagement structures for incrementally repositioning a patient's mandible and comprising occlusal blocks of any one of clauses 1-66.

Clause 68. The system of clause 67, wherein a height of the occlusal blocks for each of the plurality of orthodontic aligners is about 5 mm or about 7 mm.

Clause 69. The system of clause 67, wherein a shape of each of the occlusal blocks for each aligner of the plurality of aligners for a lower arch are the same shape.

Clause 70. The system of clause 67, wherein a shape of each of the occlusal blocks for each aligner of the plurality of aligners for an upper arch are the same shape.

Clause 71. An orthodontic treatment system comprising: a plurality of sets orthodontic aligners, each of the plurality of orthodontic aligners having: a first plurality of a teeth receiving cavities, a first engagement structure comprising a first engagement surface, and a second engagement structure comprising a second engagement surface; and a second appliance comprising: a second plurality of teeth receiving cavities, a third engagement structure comprising a third engagement surface to engage the first engagement surface, and a fourth engagement structure comprising a fourth engagement surface to engage the second engagement surface, and wherein the first and second engagement surfaces are inclined with respect to the third and fourth engagement surfaces, respectively, to generate mandibular relocation forces and limit a lateral movement of the mandible.

Clause 72. The apparatus of clause 71, further comprising the plurality of occlusal blocks, and wherein the first engagement structure comprises the first occlusal block and the third engagement structure comprises the second occlusal block.

Clause 73. The apparatus of clause 72, further comprising a third occlusal block corresponding to the first occlusal block and a fourth occlusal block corresponding the second occlusal block and wherein the second engagement structure comprises the third occlusal block and the fourth engagement structure comprises the fourth occlusal block.

Clause 74. The apparatus of clause 71, wherein the first engagement surface is inclined relative to a midline of the first engagement structure and the second engagement surface is opposingly inclined relative to a midline of the second engagement structure to limit the lateral movement of the mandible and reposition the mandible.

Clause 75. The apparatus of clause 71, wherein the third engagement surface is inclined relative to a midline of the third engagement structure and the fourth engagement surface is opposingly inclined relative to a midline of the fourth engagement structure to limit lateral movement of the mandible and reposition the mandible.

Clause 76. A plurality of occlusal blocks for a mandibular relocation, comprising: a first occlusal block comprising a first engagement surface and a first side surface; a first undercut formed in the first side surface of the first occlusal block; a first keyway formed in the first side surface of the first occlusal block; a second occlusal block comprising a second engagement surface to engage the first engagement surface and a second side surface; and a second keyway formed in the second side surface of the second occlusal block.

Clause 77. The plurality of occlusal blocks of clause 76, wherein the first side surface has a lower portion and an upper portion.

Clause 78. The plurality of occlusal blocks of clause 77, wherein the lower portion extends from a base towards an occlusal surface.

Clause 79. The plurality of occlusal blocks of clause 78, wherein the upper portion extends from the occlusal surface towards the base.

Clause 80. The plurality of occlusal blocks of clause 79, wherein the upper portion meets the lower portion along a mesial-distal line between the occlusal surface and the base.

Clause 81. The plurality of occlusal blocks of clause 80, the first side surface of the lower portion forms the undercut by extending from the base towards the upper portion at a draft angle with respect to a line perpendicular to the occlusal plane.

Clause 82. The plurality of occlusal blocks of clause 81, wherein the first side surface is a buccal side surface and the first occlusal block includes a lingual side surface, opposite the buccal side surface, the lingual side surface extending from the base at the draft angle.

Clause 83. The plurality of occlusal blocks of clause 82, wherein the draft angle is between 1 degree and 45 degrees.

Clause 84. The plurality of occlusal blocks of clause 82, wherein the draft angle is about 5 degrees.

Clause 85. A system comprising: a plurality of first and second orthodontic aligners for a plurality of stages of treatment, each of the plurality of first and second orthodontic aligners having: tooth receiving cavities for incrementally repositioning a patient's teeth from an initial position towards a final position; the plurality of first orthodontic aligners having: a first occlusal block comprising a first engagement surface and a first side surface; a first undercut formed in the first side surface of the first occlusal block; a first keyway formed in the first side surface of the first occlusal block; the plurality of second orthodontic aligners having: a second occlusal block comprising a second engagement surface to engage the first engagement surface and a second side surface; and a second keyway formed in the second side surface of the second occlusal block.

Clause 86. The plurality of occlusal blocks of clause 85, wherein the first side surface has a lower portion and an upper portion.

Clause 87. The plurality of occlusal blocks of clause 86, wherein the lower portion extends from a base towards an occlusal surface.

Clause 88. The plurality of occlusal blocks of clause 87, wherein the upper portion extends from the occlusal surface towards the base.

Clause 89. The plurality of occlusal blocks of clause 88, wherein the upper portion meets the lower portion along a mesial-distal line between the occlusal surface and the base.

Clause 90. The plurality of occlusal blocks of clause 89, the first side surface of the lower portion forms the undercut by extending from the base towards the upper portion at a draft angle with respect to a line perpendicular to the occlusal plane.

Clause 91. A system comprising: a plurality of first and second orthodontic aligners for a plurality of stages of treatment, each of the plurality of first and second orthodontic aligners having: tooth receiving cavities for incrementally repositioning a patient's teeth from an initial position towards a final position; the plurality of first orthodontic aligners having: any combination of the occlusal blocks of clauses 1-91.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A plurality of occlusal blocks for a mandibular relocation, comprising:
   a first occlusal block having a first 3D shape and comprising a first engagement surface and a first occlusal surface, the first engagement surface having a first midline extending in an occlusal-gingival direction, the first engagement surface including a first portion on a first side of the midline and a second portion on a second side of the midline, the first portion comprising a curvature different from the second portion, the first portion having a substantially straight edge between the first engagement surface and one of a buccal or lingual surface of the first occlusal block and the second portion having a convex curved edge between the engagement surface and another one of the buccal or the lingual surface of the first occlusal block; and
a second occlusal block having a second 3D shape and comprising a second engagement surface and a second occlusal surface, the second engagement surface to engage the first engagement surface and including a portion that is convex;
wherein the first engagement surface and the second engagement surface are shaped to engage each other with a curvature difference, wherein the first 3D shape and the second 3D shape are substantially the same 3D shape.

2. The plurality of occlusal blocks of claim 1, wherein the first engagement surface and the second engagement surface comprise similar shape profiles oriented in opposing directions.

3. The plurality of occlusal blocks of claim 1, wherein the first engagement surface and the second engagement surface are shaped to engage each other along an engagement line.

4. The plurality of occlusal blocks of claim 3, wherein the first engagement surface and the second engagement surface are shaped to engage each other with the curvature difference along a substantially straight line.

5. The plurality of occlusal blocks of claim 3, wherein the first engagement surface and the second engagement surface are shaped to engage each other at a locus of engagement, the locus of engagement extending along the line.

6. The plurality of occlusal blocks of claim 1, wherein a first 3D shape profile of the first engagement surface and a second 3D shape profile of the second engagement surface correspond to each other and optionally wherein the first 3D shape profile matches the second 3D shape profile.

7. The plurality of occlusal blocks of claim 1, wherein the first occlusal block and the second occlusal block correspond to replicas of each other.

8. A plurality of occlusal blocks for a mandibular relocation, comprising:
a first occlusal block comprising:
a first engagement surface having a first midline extending in an occlusal-gingival direction, and
a first occlusal surface, the first engagement surface comprising a first portion on a first side of the midline and a second portion on a second side of the midline the first portion comprising a curvature different from the second portion, the first portion having a substantially straight edge between the engagement surface and one of a buccal or lingual surface of the first occlusal block and the second portion having a convex curved edge between the engagement surface and another one of the buccal or the lingual surface of the first occlusal block; and
a second occlusal block comprising a second engagement surface and a second occlusal surface, the second engagement surface to engage the first engagement surface;
wherein the first engagement surface and the second engagement surface are shaped to engage each other with a curvature difference.

9. The plurality of occlusal blocks of claim 8, wherein the second occlusal block comprises a second midline and the second engagement surface comprises a first portion on a first side of the second midline and a second portion on a second side of the second midline, the first portion comprising a curvature different from the second portion.

10. The plurality of occlusal blocks of claim 9, wherein the first portion of the first engagement surface comprises a curvature corresponding to a curvature of the second portion of the second engagement surface and a curvature of the second portion of the first engagement surface comprises a curvature corresponding to a curvature of the first portion of the second engagement surface.

11. The plurality of occlusal blocks of claim 10, wherein each of the first portion and the second portion of the first engagement surface and the first portion and the second portion of the second engagement surface comprise convex surfaces.

12. The plurality of occlusal blocks of claim 10, wherein the curvature of the first portion of the first engagement surface matches the curvature of the second portion of the second engagement surface and the curvature of the second portion of the first engagement surface matches the curvature of the first portion of the second engagement surface.

13. The plurality of occlusal blocks of claim 10, wherein one or more of the first portion or the second portion of the first engagement surface comprises a curvature of zero and wherein one or more of the first portion or the second portion of the second engagement surface comprises a curvature of zero.

14. The plurality of occlusal blocks of claim 8, wherein a first 3D shape profile of the first engagement surface and a second 3D shape profile of the second engagement surface correspond to each other and optionally wherein the first 3D shape profile matches the second 3D shape profile.

15. The plurality of occlusal blocks of claim 8, wherein the first occlusal block and the second occlusal block correspond to replicas of each other.

16. The plurality of occlusal blocks of claim 15, wherein the first occlusal block comprises a first 3D exterior surface shape profile and the second occlusal block comprises a second 3D exterior surface shape profile and wherein the first 3D exterior surface shape profile matches the second 3D exterior surface shape profile to within 90% and optionally wherein the first occlusal block comprises a first volume and the second occlusal block comprises a second volume matching the first volume to within 90%.

17. An apparatus for a mandibular relocation, comprising:
a first appliance comprising a first engagement structure, the first engagement structure comprising a first occlusal surface and a first engagement surface facing generally anteriorly and inclined with respect to a first midline of the first engagement structure; and
a second appliance comprising a second engagement structure, the second engagement structure comprising a second occlusal surface and a second engagement surface facing generally posteriorly and inclined with respect to a second midline of the second engagement structure, the second engagement surface comprising a first portion on a first side of the second midline having a substantially straight edge between the second engagement surface and one of a buccal or lingual surface of the second engagement structure and a second portion on a second side of the second midline having a convex edge between the second engagement surface and another of a buccal or lingual surface of the second engagement structure;
wherein one or more of the first engagement surface or the second engagement surface is curved to create an engagement line in a lingual-buccal direction with engagement between the first engagement surface and the second engagement surface.

18. The apparatus for a mandibular relocation of claim 17, wherein the first appliance comprises a first layer of thermoformed material on an occlusal block to shape the first engagement structure of a first mandibular relocation appliance and wherein the second appliance comprises a second layer of thermoformed material on a second occlusal block to shape the second engagement structure of a second mandibular relocation appliance.

19. The apparatus for a mandibular relocation of claim 18, wherein the first engagement structure and the second engagement structure are arranged to engage each other with the first layer and the second layer therebetween.

20. The apparatus for a mandibular relocation of claim 19, wherein the first layer and the second layer comprise a type of polymeric material and the first occlusal block and the second occlusal block comprise the type of polymeric material.

21. The apparatus for a mandibular relocation of claim 18, comprising a first plurality of layers of thermoformed materials of the first appliance on the first engagement structure and a second plurality of layers of thermoformed material of the second appliance on the second engagement structure.

22. The apparatus for a mandibular relocation of claim 21, wherein the first plurality of layers comprises a harder layer of material between two softer layers of material and the second plurality of layers comprises the harder layer of material between the two softer layers of material, and optionally wherein the harder layer comprises a co-polyester and the softer layers of material comprise thermoplastic polyurethane.

\* \* \* \* \*